United States Patent
Whalley et al.

(10) Patent No.: US 10,190,901 B2
(45) Date of Patent: Jan. 29, 2019

(54) DOSE MEASUREMENT SYSTEM AND METHOD

(71) Applicant: Common Sensing Inc., Cambridge, MA (US)

(72) Inventors: Richard Whalley, Charlestown, MA (US); James White, Somerville, MA (US)

(73) Assignee: Common Sensing Inc., Cambridge, MA (US)

( * ) Notice: Subject to any disclaimer, the term of this patent is extended or adjusted under 35 U.S.C. 154(b) by 0 days.

(21) Appl. No.: 15/464,466

(22) Filed: Mar. 21, 2017

(65) Prior Publication Data

US 2018/0073906 A1   Mar. 15, 2018

Related U.S. Application Data

(63) Continuation of application No. 14/982,650, filed on Dec. 29, 2015, now Pat. No. 9,638,564, which is a
(Continued)

(51) Int. Cl.
*G01N 21/00* (2006.01)
*G01F 22/00* (2006.01)
(Continued)

(52) U.S. Cl.
CPC ........... *G01F 22/00* (2013.01); *A61M 5/1689* (2013.01); *A61M 5/16804* (2013.01);
(Continued)

(58) Field of Classification Search
CPC ...... G01J 3/44; G01J 3/02; G01J 3/021; G01J 3/0208; G01J 3/0264; G01J 3/42;
(Continued)

(56) References Cited

U.S. PATENT DOCUMENTS 4,286,646 A   9/1981   Tauber et al.
4,857,738 A   8/1989   Myers et al.
(Continued)

FOREIGN PATENT DOCUMENTS

DE   10 2006 047537 A1   12/2011
EP       1 920 793 A1    5/2008
(Continued)

OTHER PUBLICATIONS

U.S. Appl. No. 15/477,444, filed Apr. 3, 2017, Whalley et al.
(Continued)

*Primary Examiner* — Michael P Stafira
(74) *Attorney, Agent, or Firm* — Cooley LLP

(57) ABSTRACT

Embodiments described herein generally relate to devices, systems and methods for measuring the dose remaining in a drug delivery device that is used for delivering a dose to a patient. In some embodiments, a dose measurement system for measuring the liquid volume in a container includes a plurality of light sources which are disposed and configured to emit electromagnetic radiation toward the container. A plurality of sensors are located in the apparatus that are optically coupleable to the plurality of light sources and are disposed and configured to detect the electromagnetic radiation emitted by at least a portion of the light sources. The apparatus also includes a processing unit configured to receive data representing the portion of the detected electromagnetic radiation from each of the plurality of sensors. The processing unit is further operable to convert the received data into a signature representative of the electromagnetic radiation detected by the plurality of sensors.

16 Claims, 21 Drawing Sheets

Related U.S. Application Data continuation of application No. 14/548,679, filed on Nov. 20, 2014, now Pat. No. 9,255,830, which is a continuation of application No. PCT/US2013/041982, filed on May 21, 2013, which is a continuation-in-part of application No. 13/796,889, filed on Mar. 12, 2013, now Pat. No. 8,817,258.

(60) Provisional application No. 61/754,262, filed on Jan. 18, 2013, provisional application No. 61/649,919, filed on May 21, 2012.

(51) Int. Cl.
| | |
|---|---|
| G01F 23/284 | (2006.01) |
| G01F 13/00 | (2006.01) |
| A61M 5/168 | (2006.01) |
| G01F 11/02 | (2006.01) |
| G01F 17/00 | (2006.01) |
| G01N 21/17 | (2006.01) |
| A61M 5/31 | (2006.01) |

(52) U.S. Cl.
CPC ....... *A61M 5/16886* (2013.01); *G01F 11/021* (2013.01); *G01F 13/00* (2013.01); *G01F 17/00* (2013.01); *G01F 23/284* (2013.01); *A61M 2005/3126* (2013.01); *A61M 2205/3306* (2013.01); *A61M 2205/3379* (2013.01); *A61M 2205/70* (2013.01); *G01N 21/1702* (2013.01)

(58) Field of Classification Search
CPC ...... G01J 3/0218; G01J 3/0256; G01J 3/0272; G01J 3/0202; G01J 3/024; G01J 3/0286; G01J 3/0291; G01J 3/10; G01J 3/28
See application file for complete search history.

(56) References Cited

U.S. PATENT DOCUMENTS

| | | | |
|---|---|---|---|
| 4,904,878 A | 2/1990 | Gipp et al. | |
| 4,952,055 A | 8/1990 | Wyatt | |
| 5,065,037 A | 11/1991 | Finney et al. | |
| 5,184,510 A | 2/1993 | Rossman | |
| 5,303,585 A | 4/1994 | Lichte | |
| 5,452,076 A | 9/1995 | Schopper et al. | |
| 5,556,002 A | 9/1996 | Green | |
| 5,569,212 A | 10/1996 | Brown | |
| 5,593,390 A | 1/1997 | Castellano et al. | |
| 5,606,125 A | 2/1997 | Lyons et al. | |
| 5,628,309 A | 5/1997 | Brown | |
| 5,720,733 A | 2/1998 | Brown | |
| 5,748,091 A | 5/1998 | Kim | |
| 5,782,814 A | 7/1998 | Brown et al. | |
| 5,792,117 A | 8/1998 | Brown | |
| 5,938,642 A | 8/1999 | Burroughs et al. | |
| 6,068,615 A | 5/2000 | Brown et al. | |
| 6,090,473 A | 7/2000 | Yoshikawa et al. | |
| 6,110,148 A | 8/2000 | Brown et al. | |
| 6,113,578 A * | 9/2000 | Brown ............... | A61B 5/14532 222/23 |
| 6,270,455 B1 | 8/2001 | Brown | |
| 6,352,523 B1 | 3/2002 | Brown et al. | |
| 6,452,158 B1 | 9/2002 | Whatley et al. | |
| 6,505,509 B2 | 1/2003 | Gualtieri | |
| 6,685,678 B2 | 2/2004 | Evans et al. | |
| 7,074,209 B2 | 7/2006 | Evans et al. | |
| 7,115,113 B2 | 10/2006 | Evans et al. | |
| 7,408,632 B2 | 8/2008 | Moore et al. | |
| 7,498,563 B2 | 3/2009 | Mandro et al. | |
| 7,772,008 B2 | 8/2010 | Curtis et al. | |
| 8,079,245 B1 | 12/2011 | Owens et al. | |
| 8,197,449 B2 | 6/2012 | Nielsen et al. | |
| 8,221,356 B2 | 7/2012 | Enggaard et al. | |
| 8,348,904 B2 | 1/2013 | Petersen | |
| 8,618,485 B1 | 12/2013 | Lockhart | |
| 8,817,258 B2 | 8/2014 | Whalley et al. | |
| 9,250,111 B2 | 2/2016 | Whalley et al. | |
| 9,255,830 B2 | 2/2016 | Whalley et al. | |
| 9,638,564 B2 | 5/2017 | Whalley et al. | |
| 9,642,968 B2 | 5/2017 | Whalley et al. | |
| 2001/0056258 A1 | 12/2001 | Evans | |
| 2004/0089067 A1 | 5/2004 | Frank | |
| 2005/0177137 A1 | 8/2005 | Kipfer | |
| 2006/0154327 A1 | 7/2006 | Bachur, Jr. et al. | |
| 2006/0178578 A1 | 8/2006 | Tribble et al. | |
| 2007/0143062 A1 | 6/2007 | Memmott et al. | |
| 2007/0213949 A1 | 9/2007 | Artiuch | |
| 2008/0108885 A1 | 5/2008 | Colvin, Jr. | |
| 2008/0113337 A1 | 5/2008 | Sakudo et al. | |
| 2008/0316612 A1 | 12/2008 | Hyde et al. | |
| 2009/0159654 A1 | 6/2009 | Grimard | |
| 2009/0299279 A1* | 12/2009 | Richter ................. | A61M 5/24 604/93.01 |
| 2010/0030136 A1 | 2/2010 | Dacquay et al. | |
| 2010/0080086 A1 | 4/2010 | Wright et al. | |
| 2010/0134303 A1 | 6/2010 | Perkins | |
| 2010/0213392 A1 | 8/2010 | Hatzav et al. | |
| 2011/0102796 A1 | 5/2011 | Shang et al. | |
| 2011/0184343 A1 | 7/2011 | Veit et al. | |
| 2011/0270214 A1 | 11/2011 | Joergensen et al. | |
| 2011/0292399 A1* | 12/2011 | Alphonse ........... | G01B 9/02044 356/479 |
| 2011/0313395 A1 | 12/2011 | Krulevitch et al. | |
| 2012/0234074 A1 | 9/2012 | Hagen | |
| 2012/0268741 A1 | 10/2012 | Pommereau et al. | |
| 2013/0030405 A1 | 1/2013 | Hartman et al. | |
| 2014/0130745 A1 | 5/2014 | Van Halsema et al. | |
| 2015/0115158 A1 | 4/2015 | Fu et al. | |
| 2015/0362350 A1 | 12/2015 | Miller et al. | |
| 2016/0030673 A1 | 2/2016 | White et al. | |
| 2016/0061646 A1 | 3/2016 | Mestivier et al. | |
| 2018/0050157 A1 | 2/2018 | Whalley et al. | |
| 2018/0064881 A1 | 3/2018 | Whalley et al. | |

FOREIGN PATENT DOCUMENTS

| | | |
|---|---|---|
| JP | 2000-279515 A | 10/2000 |
| WO | WO 2010/098929 A1 | 9/2010 |
| WO | WO 2011/108225 A1 | 9/2010 |
| WO | WO 2011/032960 A1 | 3/2011 |
| WO | WO 2011/084713 A1 | 7/2011 |
| WO | WO 2012/062843 A1 | 5/2012 |
| WO | WO 2012/126975 A1 | 9/2012 |

OTHER PUBLICATIONS

U.S. Appl. No. 15/649,224, filed Jul. 13, 2017, Whalley et al.
Extended European Search Report dated Jun. 7, 2016 from European Application No. 13793067.3, 21 pages.
International Search Report and Written Opinion dated Oct. 21, 2013 from International Application No. PCT/US2013/041982, 10 pages.
Office Action dated Feb. 28, 2017 from U.S. Appl. No. 13/796,889, 10 pages.
Office Action dated Jun. 10, 2015 from U.S. Appl. No. 14/334,181, 12 pages.
Office Action dated Jun. 15, 2016 from U.S. Appl. No. 14/982,650, 11 pages.
Office Action dated Jun. 17, 2016 from U.S. Appl. No. 14/982,668, 10 pages.
Office Action dated Jun. 28, 2016 from Chinese Application No. 201380036003.4 w/English language translation, 19 pages.
Office Action dated Apr. 12, 2017 from Chinese Application No. 201380036003.4 w/English language translation, 15 pages.
Communication pursuant to Article 94(3) dated Jan. 31, 2018 issued by the European Patent Office from European Application No. 13793067.3, 6 pages.
International Search Report and Written Opinion dated Nov. 17, 2017 from International Application No. PCT/US2017/041982, 15 pages.

(56) References Cited

OTHER PUBLICATIONS

Non-Final Office Action dated Feb. 14, 2018 from U.S. Appl. No. 15/649,224, 15 pages.
Decision of Rejection dated Nov. 1, 2017 from Japanese Application No. 2015-514106, w/English translation, 13 pages.
Extended European Search Report dated Mar. 8, 2018 from European Application No. 15826907.6, 10 pages.
International Search Report and Written Opinion dated Nov. 20, 2015 for International Application No. PCT/US2015/043417, 8 pages.
Non-Final Office Action dated Feb. 28, 2014 from U.S. Appl. No. 13/796,889, 10 pages.
Non-Final Office Action dated Jun. 29, 2018 from U.S. Appl. No. 14/816,634, 15 pages.
Non-Final Office Action dated Jul. 25, 2018 from U.S. Appl. No. 15/477,444, 13 pages.
Non-Final Office Actions dated Jun. 10, 2015 from U.S. Appl. No. 14/334,181, 12 pages.
Notice of Reasons for Rejection dated Feb. 17, 2017 from Japanese Application No. 2015-514106 w/English translation, 15 pages.
Office Action dated Mar. 27, 2018 from Chinese Application No. 20130036003.4 w/English translation, 7 pages.

\* cited by examiner

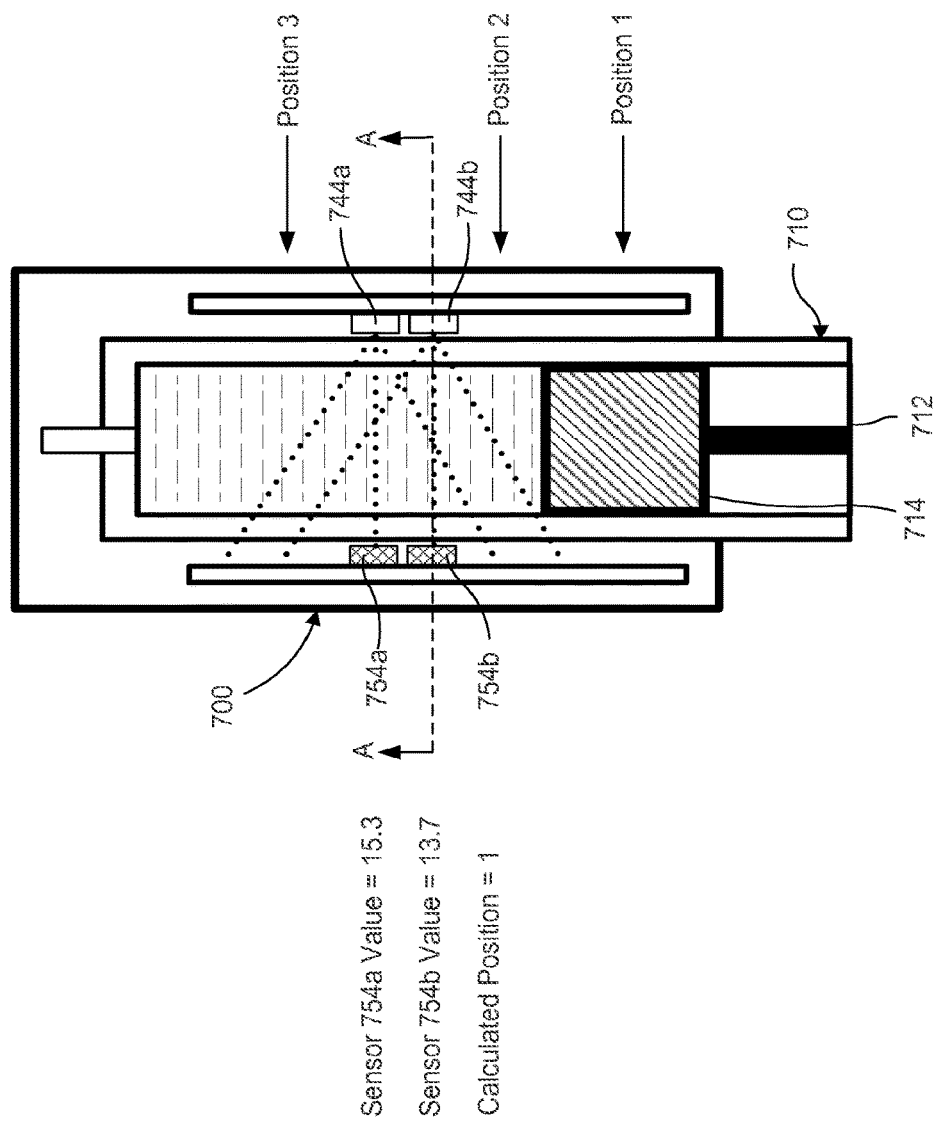

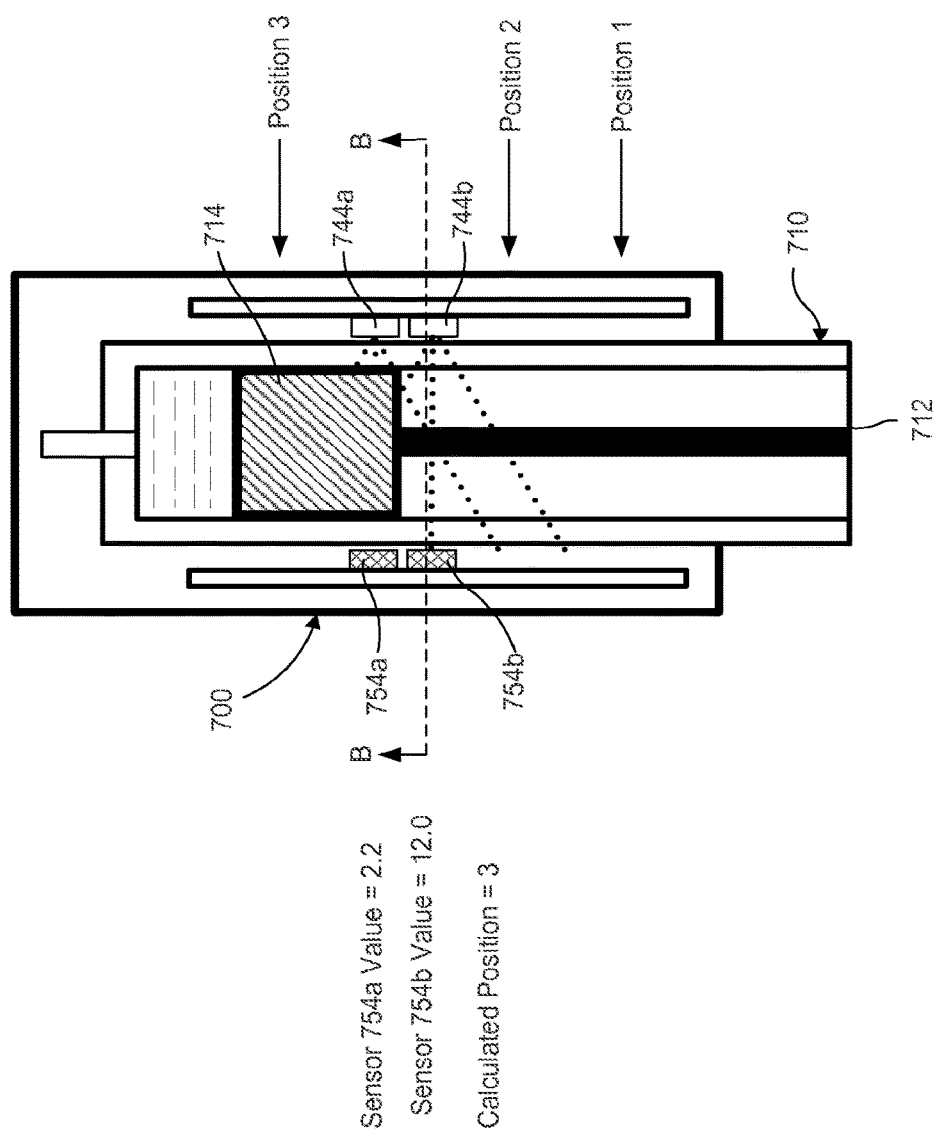

DOSE MEASUREMENT SYSTEM AND METHOD

CROSS-REFERENCE TO RELATED APPLICATIONS

This application is a continuation of U.S. patent application Ser. No. 14/982,650, filed Dec. 29, 2015, entitled "Dose Measurement System and Method," now U.S. Pat. No. 9,638,564, which is a continuation of U.S. patent application Ser. No. 14/548,679, filed Nov. 20, 2014, entitled "Dose Measurement System and Method," now U.S. Pat. No. 9,255,830, which is a continuation of International Patent Application No. PCT/US2013/041982, filed May 21, 2013, entitled "Dose Measurement System and Method," which is a continuation-in-part of U.S. patent application Ser. No. 13/796,889, filed Mar. 12, 2013, entitled "Dose Measurement System and Method," now U.S. Pat. No. 8,817,258, which claims priority to and the benefit of U.S. Provisional Application No. 61/754,262, filed Jan. 18, 2013, entitled "Non-Invasive Injection Pen and Syringe Sensor Device," and U.S. Provisional Application No. 61/649,919, filed May 21, 2012, entitled "Non-Invasive Injection Pen and Syringe Sensor Device," all of which are hereby incorporated by reference in their entirety.

BACKGROUND

Embodiments described herein relate generally to devices, systems and methods for measuring the dose remaining in a drug delivery device.

Many chronic disease patients are prescribed medications that need to be self administered using injection pens or similar drug delivery devices. For example, patients diagnosed with Type I or II diabetes need to regularly check their blood glucose levels and self administer an appropriate dose of insulin using an injection pen. In order to monitor the efficacy of the medication, dose information needs to be recorded. The process of manually logging dose information, particularly in an uncontrolled setting, is tedious and error prone. Patients often forget to log the dose information when administering medicine. In addition, many such patients can be minors or elderly and cannot efficiently keep track of the dose information.

Incomplete dosage records hinder the ability of the patient to self-manage disease conditions and prevent caretakers from adjusting care plans through behavioral insight. Lack of adherence to target dosage schedules for injectable medicine can result in an increased need for critical care, which results in a significant increase in health care costs in countries around the world.

Thus, there is a need for better technological aids to assist patients in improving their ability to self-manage disease treatment. Such aids can not only make the patients more aware and educated about their health condition, but also assist caregivers in better monitoring patient health. In particular, there is a need for systems, devices and methods that facilitate data acquisition on patient behavior and that allow that data to be used to reduce the incidence of hospital visits (e.g., readmission), as well as to inform and educate patients, care providers, family and financial service providers.

SUMMARY

Embodiments described herein relate generally to devices, systems and methods for measuring the dose remaining in a drug delivery device. In some embodiments, a dose measurement system for measuring the liquid volume in a container includes a plurality of light sources which are disposed and configured to emit electromagnetic radiation toward the container. A plurality of sensors are optically coupleable to the plurality of light sources and are disposed and configured to detect the electromagnetic radiation emitted by at least a portion of the light sources. The apparatus also includes a processing unit configured to receive data representing the portion of the detected electromagnetic radiation from each of the plurality of sensors and to convert the received data into a signature representative of the electromagnetic radiation detected by the plurality of sensors.

BRIEF DESCRIPTION OF THE DRAWINGS

FIG. 11A-11C are cross-section views of an embodiment of a dose measurement system, in a first, second and third configuration, respectively.

DETAILED DESCRIPTION

Figure 1:
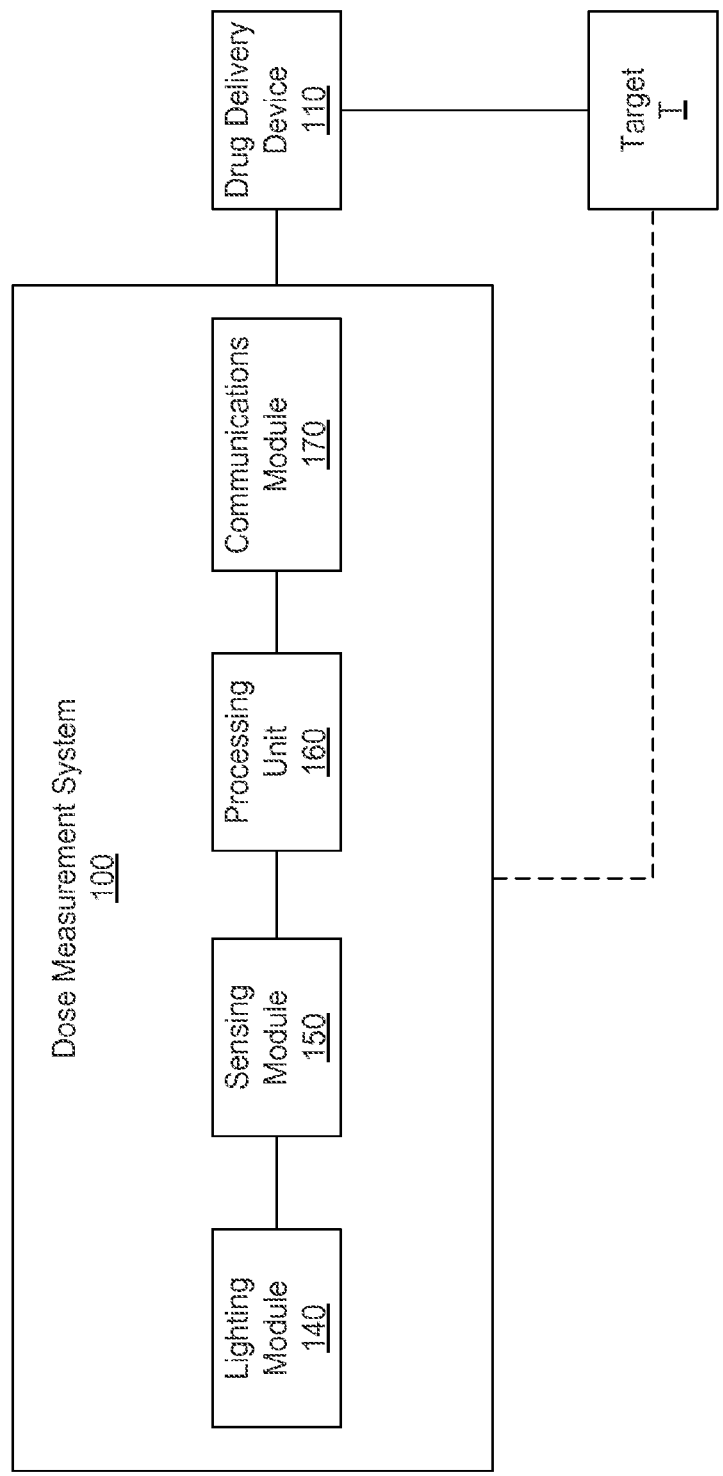
FIG. 1 is a schematic block diagram of a dose measurement system, according to an embodiment.

Embodiments described herein relate generally to devices, systems and methods for measuring the dose remaining in a drug delivery device. In some embodiments, a dose measurement system for measuring the liquid volume in a container includes a plurality of light sources which are disposed and configured to emit electromagnetic radiation toward the container. A plurality of sensors are optically coupleable to the plurality of light sources and are disposed and configured to detect the electromagnetic radiation emitted by at least a portion of the light sources. The apparatus also includes a processing unit configured to receive data representing the portion of the detected electromagnetic radiation from each of the plurality of sensors and to convert the received data into a signature representative of the electromagnetic radiation detected by the plurality of sensors.

In some embodiments, a method of estimating a volume of liquid in a drug delivery device includes causing a plurality of light sources to emit electromagnetic radiation toward a drug container and detecting a signature of the emitted electromagnetic radiation through the drug container with a plurality of sensors. The detected signature is then compared to a plurality of reference signatures to determine the volume of liquid in the drug container. Each of the plurality of reference signatures correspond to a volume level remaining in the drug container. In some embodiments, detecting the signature of the emitted electromagnetic radiation through the drug container includes detecting at least a portion of the electromagnetic radiation emitted from at least a portion of the plurality of light sources. The portion of the electromagnetic radiation detected by each of the plurality of sensor devices can be compiled into the signal signature.

In some embodiments, the method also includes calculating a dose delivered to a patient based on the volume of liquid in the drug container. In some embodiments, the dose delivered to a patient is compared with a patient medication schedule to monitor compliance. The method can further include correcting the signal signature for background light which can contribute to noise. The correction can include comparing the signal signature with a background signature detected by the plurality of sensors in a dark state of each of the plurality of light sources. In some embodiments, the method also includes generating the plurality of reference signatures by recording the signature for a range of dose volumes in the drug container. The method can also include associating the signal with the reference signature using probabilistic matching to determine the volume of liquid remaining in the dose container.

In some embodiments, a method for determining a dose delivered by an injection pen using the drug measurement system includes causing a plurality of light sources to emit electromagnetic radiation toward the injection pen a first time and detecting a first signature of the emitted electromagnetic radiation through the injection pen with a plurality of sensors. The first signature is then compared to a plurality of reference signatures to determine the first volume of liquid in the injection pen. The method further includes causing the plurality of light sources to emit electromagnetic radiation toward the injection pen a second time, after the first time, and detecting a second signature of the emitted electromagnetic radiation through the injection pen with the plurality of sensors. The second signature is then compared to the plurality of reference signatures to determine the second volume of liquid in the injection pen. The second volume can be deducted from the first volume to determine a dose delivered from the injection pen.

In some embodiments, the plurality of light sources and the plurality of sensor are disposed in an injection pen cap. In some embodiments, the method includes detecting the first signature prior to the injection pen cap being removed from the injection pen and detecting the second signature after the injection pen cap has been placed back on the injection pen. The method can also include communicating the dose delivered information to an external device. In some embodiments, the method includes switching the pen cap to a power save mode after a predetermined period of inactivity of the pen cap. In some embodiments, the method further includes alerting the user if a volume of liquid remaining in the drug container is critically low and/or if it is time to deliver a dose of medication.

In some embodiments, a health management system includes a drug delivery device including a drug reservoir, and a dose measurement system configured to be removably coupleable to the drug delivery device. The dose measurement system includes a plurality of light sources disposed and configured to emit electromagnetic radiation toward the drug reservoir a plurality of sensors optically coupleable to the plurality of light sources disposed and configured to detect a quantity of electromagnetic radiation communicated through the drug reservoir. The quantity of electromagnetic radiation serves as a signature representative of the volume of liquid remaining in the drug reservoir. The health management system also includes a display configured to present information to a user indicative of the volume of liquid remaining in the drug reservoir. The dose measurement system can be configured to communicate data representative of the volume of liquid remaining in the drug reservoir to a remote device, for example, to allow the remote device to calculate a dose delivered to the patient. In some embodiments, the dose management system is configured to receive user health data from the remote device which can include, for example user blood glucose level, user diet, user exercise, and/or user home health monitored data.

As used in this specification, the terms "about" and "approximately" generally include plus or minus 10% of the value stated. For example, about 5 would include 4.5 to 5.5, approximately 10 would include 9 to 11, and about 100 would include 90 to 110.

FIG. 1 is a schematic block diagram of a dose measurement system 100 for measuring the dose in a drug delivery device 110. The dose measurement system 100 includes a lighting module 140, a sensing module 150, a processing unit 160 and a communications module 170. The dose measurement system 100 can be configured to be removably coupleable to the drug delivery device 110 that is used to deliver a drug dose to a target T such as, for example, a human patient.

The drug delivery device 110 can be any drug delivery device 110 that can be used for injecting a medication into a patient. For example, the drug delivery device 110 can be an injection pen (e.g., insulin injection pen), a syringe, pump (e.g., insulin delivery pump), an ampoule, or a vial. The dose measurement system 100 can be configured to be coupleable to a wide variety of drug delivery devices 110, e.g., different shapes, sizes, and drug volumes. In some embodiments, the dose measurement system 100 can be configured to receive a portion of the drug delivery device 110, e.g., a portion that defines an internal volume containing the drug, an injector, and/or plunger. In some embodiments, the dose measurement system 100 is configured to be removable from the drug delivery device 110 when the user is delivering a dose to the target T. In some embodiments, the dose measurement system 110 can remain attached to the drug delivery device 110 when the user is delivering a dose to the target T. In some embodiments, the dose measurement system 100 is configured to be reusable. In some embodiments, the dose measurement system 110 can be permanently coupled to the drug delivery device 110, for example, integrated into the body of the drug delivery device. In such embodiments, the dose measurement system 100 can be disposable.

The lighting module 140 includes a plurality of light sources configured to emit electromagnetic radiation towards the drug delivery device 110. In some embodiments, the plurality of light sources can be configured to emit electromagnetic radiation towards a drug reservoir (not shown) of the drug delivery device 110. In some embodiments, each of the plurality of light sources can be a light emitting diode (LED). In some embodiments, the plurality of light sources can be configured to emit infrared radiation or microwave radiation, such that the electromagnetic radiation can penetrate through a housing and any internal components of the drug delivery device 110, and/or the liquid drug contained therein. In some embodiments, the plurality of light sources can be configured to emit continuous electromagnetic radiation for a predefined time period. In some embodiments, the plurality of light sources can be configured to emit pulses of electromagnetic radiation, e.g., a series of less than 100 microsecond pulses.

The sensing module 150 includes a plurality of sensors that are optically coupleable to the plurality of light sources of the lighting module 140. In some embodiments, the each of the plurality of sensors can be a photodetector. The plurality of sensors are disposed and configured to detect the electromagnetic radiation emitted by at least a portion of the light sources. In some embodiments, the detected electromagnetic radiation includes transmitted, refracted and reflected portions of the electromagnetic radiation. In some embodiments, the refracted electromagnetic radiation can include multi-directional refraction caused by a lensing effect of a curved surface of the housing of the drug delivery device 110 and/or the drug reservoir.

The processing unit 160 is configured to receive the electromagnetic radiation signal from the sensing module 150 (i.e., each of the plurality of sensors) and convert the received data into a signal signature representative of the electromagnetic radiation detected by each of the plurality of sensors. The processing unit 160 can include a processor, e.g., a microcontroller, a microprocessor, an ASIC chip, an ARM chip, an analog to digital convertor (ADC), or a programmable logic controller (PLC). In some embodiments, the processing unit 160 can include a memory that is configured to temporarily store at least one of the electromagnetic radiation data detected by each of the plurality of sensors and the signal signature produced from it. In some embodiments, the memory can also be configured to store a plurality of reference signatures. Each of the plurality of reference signatures can be representative of a drug volume in the drug delivery device 110. In some embodiments, the processing unit 160 can also include an RFID chip configured to store information e.g., the dose remaining information, and allow a near field communication (NFC) device to read the stored information. In some embodiments, the processing unit 160 can be configured to associate the signal signature with the reference signature to determine the dose volume remaining in and/or dose injected by the drug delivery device 110. In some embodiments, the processing unit 160 can also be configured to determine the type of drug delivery device 110 coupled to the dose measurement system 100, and/or the drug contained in the drug delivery device 110. In some embodiments, the processing unit 160 can also include a global positioning system (GPS) e.g., to determine a current location of the dose measurement system 100.

The communications module 170 can be configured to allow two-way communication with an external device e.g., a smart phone app, a local computer and/or a remote server. In some embodiments, the communications module 170 includes a communication interface to provide wired communication with the external device, e.g., a USB or firewire interface. In some embodiments, the communication interface can also be used to recharge a power source (not shown), e.g., a rechargeable battery. In some embodiments, the communications module 170 can include means for wireless communication with the external device, e.g., Wi-Fi, Bluetooth®, low powered Bluetooth®, Zigbee and the like.

In some embodiments, the communications module 170 can include a display configured to communicate a status of the dose measurement system 100 to the user e.g., dose remaining, history of use, remaining battery life, wireless connectivity status and/or user reminders. In some embodiments, the status can also include information on whether an injector, for example, a needle is attached/detached to the drug delivery device 110. Generally a user is required to attach a new injector (e.g., needle) to the drug delivery device 110 prior to each drug injection. Status information on the injector attachment/detachment can therefore inform the user and/or an external monitor (e.g., a doctor) whether the user is replacing the injector after each injection.

In some embodiments, the communications module 170 can also include microphones and/or vibration mechanisms to convey audio and tactile alerts. In some embodiments, the communications module 170 can include a user input interface, e.g., a button, a switch, an alphanumeric keypad, and/or a touch screen, for example, to allow a user to input information into the dose measurement system 100, e.g., power ON the system, power OFF the system, reset the system, manually input details of a patient behavior, manually input details of drug delivery device 110 usage and/or manually initiate communication between the dose measurement system 100 and a remote device.

The dose measurement system 100 can be disposed in a housing (not shown) that can be configured to be removably coupleable to the drug delivery device 110. For example, the lighting module 140, sensing module 150, processing unit 160 and the communications module 170 can be incorporated into a housing, or individual components of the dose measurement system 100 (e.g., the lighting module 140 and the sensing module 150) can be incorporated into a first housing and other components (e.g., the processing unit 160 and communications module 170) can be separate or incorporated into a second housing. In some embodiments, the housing can be configured (e.g., shaped and sized) to be removably coupled to at least a portion of the drug delivery device 110. For example, the housing can have a recess and/or define a bore into which a portion of the drug delivery device 110 can be received. The housing can have alignment features to allow the dose measurement system 100 to be coupled to the drug delivery device 110 in a predetermined radial orientation. The housing can be opaque and include an insulation structure to prevent interference from ambient electromagnetic radiation, e.g., to increase signal quality. For example, the insulation structure can be a metal lining configured to shield the electronic components of the dose measurement system 100 from external electromagnetic radiation. In some embodiments, the housing can substantially resemble a pen cap, e.g., to act as a replacement cap for the drug delivery device 110 (e.g., an injection pen).

In some embodiments, the lighting module 140 and the sensing module 150 can be disposed and oriented in the housing of the dose measurement system 100, such that the plurality of light sources are disposed on a first side, and the plurality of sensors are disposed on a second side of the drug delivery device 110. In some embodiments, the plurality of light sources can be disposed at a first radial position with respect to the drug delivery device 110 and the plurality of sensors can be disposed at a second radial position which is different than the first radial position, e.g., the second radial position is approximately 180 degrees from the first radial position. In other words, the dose management system 100 can be arranged so that the plurality of light sources can be disposed on one side of a drug reservoir and the plurality of sensors can be disposed on the opposite side of the drug reservoir. In some embodiments, each of the plurality of light sources and the plurality of sensors can be disposed in a substantially straight line. In some embodiments, the plurality of light sources are disposed such that each light source is located adjacent to at least one sensor, each light source also located parallel to and in line of sight of at least one sensor. In some embodiments, at least one of the plurality of light sources and/or at least one of the plurality of sensors can be located in an inclined orientation with respect to a longitudinal axis of the drug delivery device 110. In some embodiments, the number of the plurality of sensors can be equal to, greater than or less than the number of the plurality of light sources. In some embodiments, the plurality of light sources and the plurality of sensors can be configured such that the dose measurement system 110 can detect the volume of drug in the drug delivery device 110 with a resolution of 1 unit of drug or smaller (e.g., fractions of units of drug such as 0.1 units, 0.2 units, 0.5 unites, etc.). In some embodiments, the plurality of light sources and the plurality of sensors can be configured such that the dose measurement system 110 can detect the position of a plunger portion of an actuator disposed in the drug delivery device 110 with a resolution of 10 micrometers, 20 micrometers, 30 micrometers, 40 micrometers, 50 micrometers, 60 micrometers, 70 micrometers, 80 micrometers, 90 micrometers, 100 micrometers, 110 micrometers, 120 micrometers, 130 micrometers, 140 micrometers, 150 micrometers, 160 micrometers, 170 micrometers, 180 micrometers, or 200 micrometers, inclusive of all ranges therebetween.

Having described above various general principles, several exemplary embodiments of these concepts are now described. These embodiments are only examples, and many other configurations of a dose measurement system, systems and/or methods for measuring dose delivered by a drug delivery device and overall health of a patient are envisioned.

Figure 2:
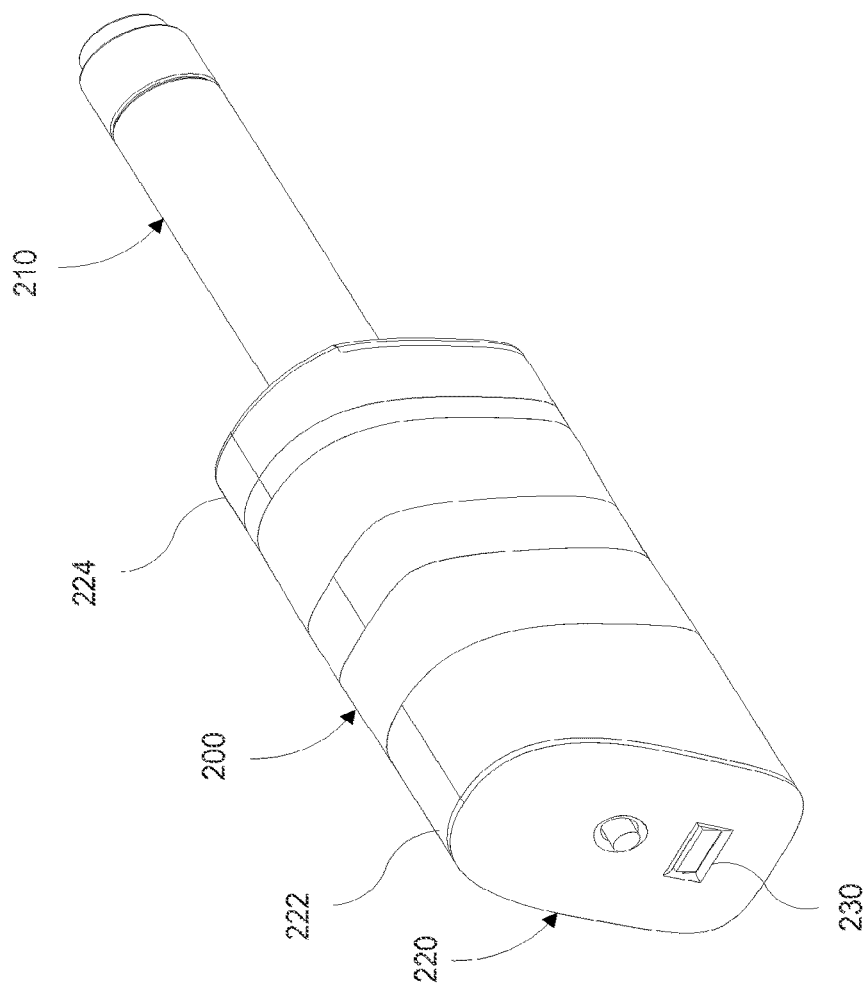
FIG. 2 is a perspective view of a dose measurement system, according to an embodiment.
Figure 3:
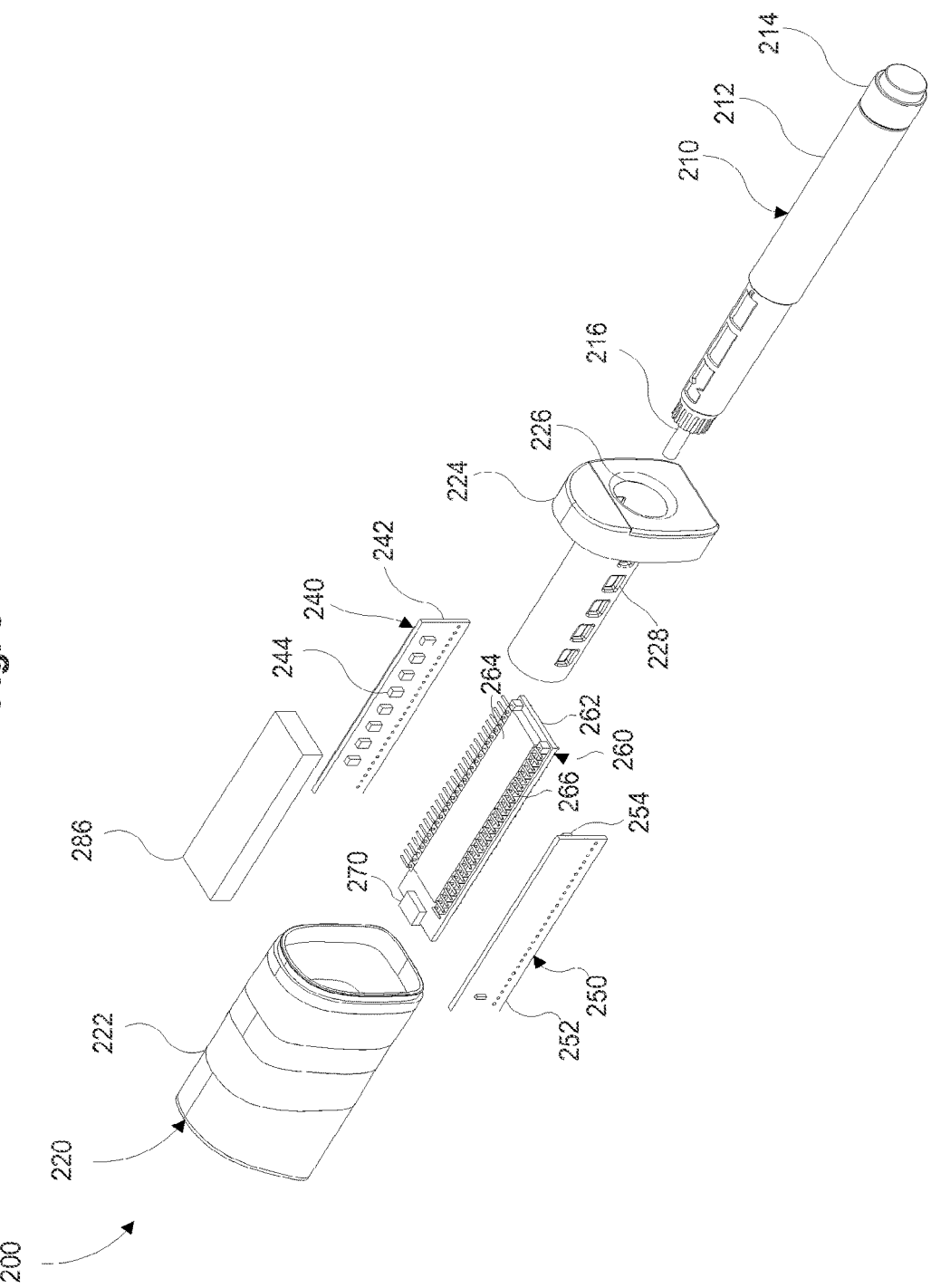
FIG. 3 is an exploded perspective view of the dose measurement system of FIG. 2.
Figure 4:
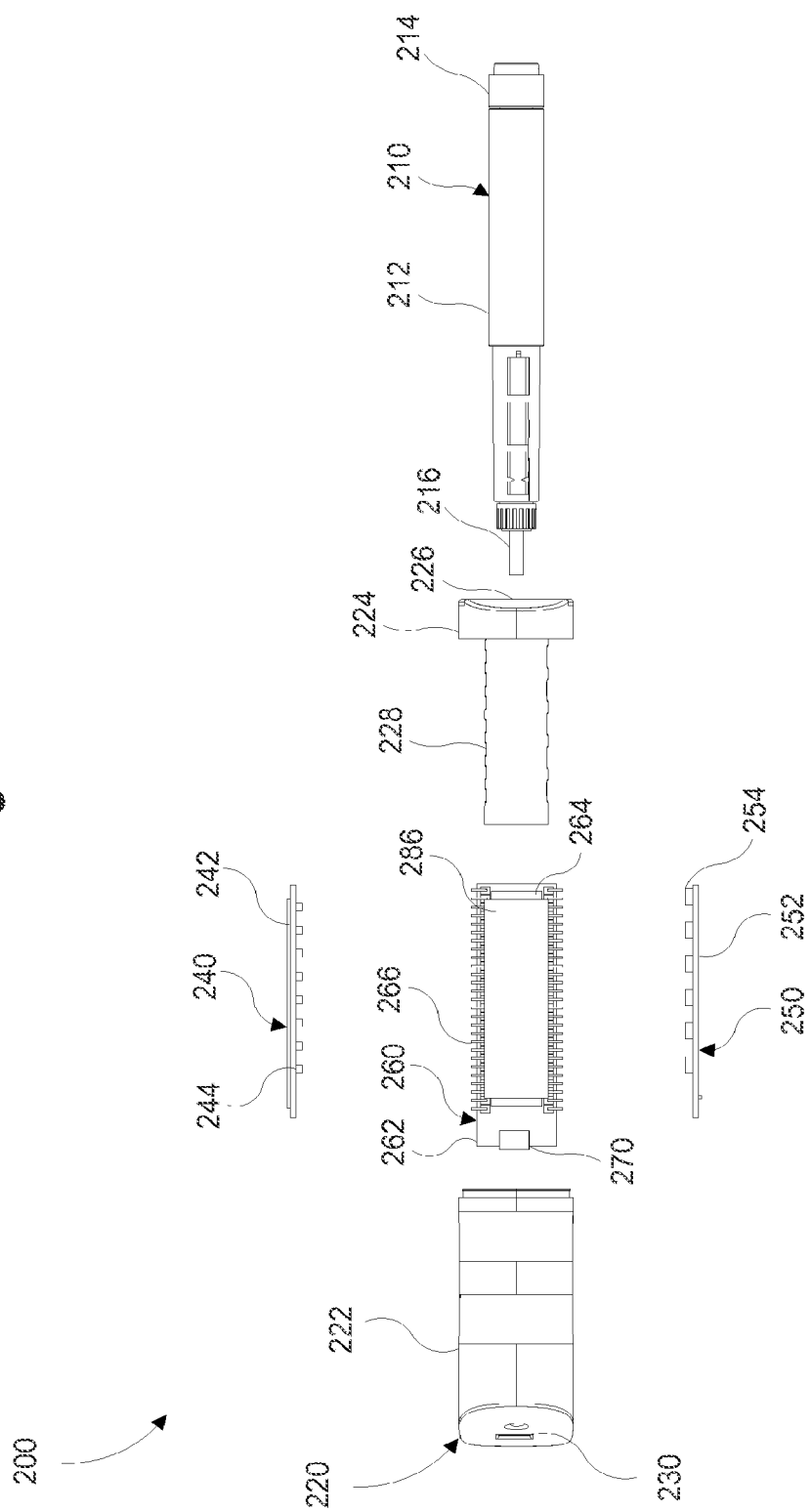
FIG. 4 is a top exploded top view of the dose measurement system of FIG. 2.

Referring now to FIGS. 2-4 a dose measurement system 200 can include a lighting module 240, a sensing module 250, a processing unit 260, a communications module 270 and a power source 286. The dose measurement system 200 can be configured to be removably coupleable to a drug delivery device 210 (also referred to herein as "an injection pen 210"). The drug delivery device 210 can be configured to deliver a predefined quantity of a drug (e.g., dose) to a patient. Examples of the drug delivery device 210 include insulin injection pens that can be used by a patient to self administer insulin. As described herein, the drug delivery device 210 can include a housing 212, an actuator 214 and an injector 216. The housing 212 can be relatively opaque, such that it only allows select wavelengths of electromagnetic radiation to be transmitted therethrough, e.g., infrared or microwave radiation. The housing 210 defines an internal volume (e.g., reservoir) for storing a drug. The actuator 214 can include a plunger portion in fluid communication with the drug and configured to communicate a predefined quantity of drug to the patient. The actuator 214 can be configurable, e.g., by the user, to dispense variable quantities of the drug. The injector 216 is configured to penetrate a user's skin for intramuscular, subcutaneous, and/or intravenous delivery of the drug.

The dose measurement system 200 includes a housing 220 that includes a top housing portion 222 (also referred to herein as "top housing 222") and a bottom housing portion 224 (also referred to herein as "bottom housing 224"). The top housing portion 222 and the bottom housing portion 224 can be removably or fixedly coupled together by, e.g., gluing, hot welding, a snap-fit mechanism, screwed together, or by any other suitable coupling means. The housing 220 can be made from a rigid, light weight, and opaque material, e.g., polytetrafluoroethylene, high density polyethylene, polycarbonate, other plastics, acrylic, sheet metal, any other suitable material or a combination thereof. The housing 220 can also be configured to shield the internal electronic components of the dose measurement system 200 from environmental electromagnetic noise. For example, the housing can include an insulation structure (not shown) such as, for example, lined with aluminum or any other metal sheet or foil that can serve as an electromagnetic shield.

As shown in FIG. 3, the top housing portion 222 defines an internal volume for substantially housing the lighting module 240, the sensing module 250, the processing unit 260, the communications module 270 and the power source 286. The bottom housing portion 224 defines a bore 226, shaped and sized to receive at least a portion of the drug delivery device 210. For example, the bore 226 can be shaped and sized to receive only the drug containing portion of the housing 212 and the injector 216. The bore 226 can be configured to receive the drug delivery device 210 in a preferred orientation, e.g., a preferred radial orientation. In some embodiments, the bore 226 can be in close tolerance with the diameter of the drug delivery device 210, e.g., to form a friction fit with the drug delivery device 210. In some embodiments, the bore 226 can include notches, grooves, detents, any other snap-fit mechanism, or threads, for removably coupling the drug delivery device 210 to the bottom housing 224. In some embodiments, bottom housing portion 224 can include alignment features to allow the drug delivery device 210 to be coupleable with the dose measurement system 200 in a predetermined radial orientation.

In some embodiments, the bottom housing 224 can include apertures 228 for receiving at least a portion of the plurality of light sources 244 of the lighting module 240, and/or sensors 254 of the sensing module 250. The apertures 228 can be configured to provide mechanical support for the light sources 244 and/or sensors 254, or can serve as an alignment mechanism for the lighting module 240 and/or sensing module 250.

As shown in FIG. 4, the top housing 222 includes an opening 230 for receiving at least a portion of the communications module 270 such as, for example, a communication interface to provide wired communication with an external device, and/or an interface for charging the power source 286. In some embodiments, the top housing 222 can also include features, e.g., recesses, apertures, cavities, etc. for receiving a portion of the drug delivery device 210 such as, e.g., the injector 216. In some embodiments, the housing 220 can also include a detection mechanism (not shown) to detect if the drug delivery device 210 has been coupled to the dose measurement system 200, e.g., a push switch, a motion sensor, a position sensor, an optical sensor, a piezo-electric sensor, an impedance sensor, or any other suitable sensor. The housing 220 can be relatively smooth and free of sharp edges. In some embodiments, the housing 220 can be shaped to resemble a pen cap that has a form factor that occupies minimal space, e.g., can fit in the pocket of a user. In some embodiments, the housing 220 can also include features, e.g., clips for attaching to a user's shirt pocket, and/or other ornamental features. In some embodiment, the dose measurement system 200 can also serve as a replacement cap for the drug delivery device 210. In some embodiments, the housing 220 can also include sensors (e.g., optical sensors) to determine a status of the drug delivery device 210, for example, if the injector 216 (e.g., a needle) is attached/detached to the drug delivery device 210.

Referring still to FIGS. 3 and 4, the plurality of light sources 244 (e.g., LEDs) of the lighting module 240 are mounted on, or otherwise disposed on, a printed circuit board (PCB) 242. The PCB 242 can be any standard PCB made by any commonly known process. In some embodiments, the plurality of light sources 244 can be arranged in a straight line and equally spaced such that, when the portion of the drug delivery device 210 that defines the internal volume of the housing 212 holding the drug is coupled with the dose measurement system 200, the light sources 244 can illuminate the entire internal volume. In some embodiments, the light sources 244 can be placed in any other configuration, e.g., a zig zag pattern, unequally spaced, staggered orientation, alternately disposed with the sensors 254, or any other configuration as described herein.

In some embodiments, the light sources 244 can be configured to produce an electromagnetic radiation of a wavelength that is capable of penetrating through the housing 212 of the drug delivery device 210, the drug contained therein, and/or a portion of the housing 220. For example, infrared radiation or microwave radiation can penetrate many of the plastic materials that are commonly used in manufacturing drug delivery devices (e.g., injection pens). In some embodiments, an electromagnetic radiation has a frequency that can also penetrate through the internal components of the drug delivery device 210, e.g., the plunger portion of the actuator 214. In some embodiments, the light sources 244 can be configured to produce a wide beam of electromagnetic radiation, e.g., wide angled LEDs. Said another way, the electromagnetic radiation cone of a single light source 244 can have a wide angle and the electromagnetic radiation cones of adjacent light sources 244 can overlap. In some embodiments, the plurality of light sources 244 can be configured to emit pulses of electromagnetic radiation, e.g., a series of less than 100 microsecond pulses.

The plurality of sensors 254 of the sensing module 250 are mounted on, or otherwise disposed on, a PCB 252. The PCB 252 can be any standard PCB made by any commonly known process. The plurality of sensors 254 can be any optical sensors (e.g., photodiodes) optically coupleable with the plurality of light sources 244 and configured to detect at least a portion of the electromagnetic radiation emitted by the plurality of light sources 244. The electromagnetic radiation can be transmitted radiation, refracted radiation (e.g., refracted through air, drug, and/or body of drug delivery device 210), reflected radiation (e.g., reflected from a wall of the housing 220 or internally reflected from a wall of the drug delivery device 210), or multi-directional refraction/reflection caused by a lensing effect of a curved surface of the housing 212 and/or the drug reservoir. The transmitted, refracted, and reflected electromagnetic signal received by the plurality of sensors 254 can be used to create a signal signature (e.g., by the processing unit 260). For example, the signal signature can then be associated with a reference signature to determine the dose remaining in the drug delivery device 210. In some embodiments, the signal response of the sensors 254 can be used to measure usability metrics such as, for example, determining the presence of the injector 216 of the drug delivery device 210, and/or determining whether the drug delivery device 210 is coupled/uncoupled to the dose measurement system 200. In some embodiments, the signal response of the sensors 254 can also be used to determine the type of a drug delivery device 210 is coupled to the dose measurement system 200, and/or the type of drug present in the drug delivery device 210.

In some embodiments, the sensors 254 can be arranged in a substantially similar configuration to the light sources 244. In some embodiments, the number of sensors 254 can be greater or less than the number of light sources 244. In some embodiments, the light sources 244 and sensors 254 can be arranged such that each PCB 244, 254 includes a combination of light sources 244 and sensor 254, e.g., arranged alternatively. In some embodiments, the light sources 244 and/or sensors 254 can be arranged in an inclined orientation.

The processing unit 260 can include a PCB 262 and a processor 264. The PCB 262 can be any standard PCB made by any commonly known process and can include amplifiers, transistors and/or any other electronic circuitry as necessary. The processor 264 can be any processor, e.g., a microprocessor, a microcontroller, a PLC, an ASIC chip, an ARM chip, an ADC, or any other suitable processor. The processing unit 260 can be coupled to the lighting module 240 and the sensing module 250 using electronic couplings 266, such that the lighting module 240 and the sensing module 250 are oriented perpendicular to the processing unit 260 and parallel to each other. In some embodiments, the processing unit 260 can include an onboard memory for at least temporarily storing a signal signature, a reference signature database, dose information, user health data (e.g., blood glucose level), device location data (e.g., from a GPS optionally included in the dose measurement system 200 or from another GPS enabled device that is paired with the system 200 such as a blood glucose meter or cellular phone), and any other data as might be useful for a patient to manage their health. In some embodiments, the processing unit 260 can include an RFID chip configured to store information and allow an NFC device to read the information stored therein. The processing unit 260 can be configurable to control the operation of the dose measurement system 200, for example, activation and timing of the light sources 244, and/or reading and processing of electromagnetic radiation data from the sensors 254. For example, the processing unit 260 can be configured to compare electromagnetic radiation signal signature obtained form the plurality of sensors 254 and associate it with the reference signature database to determine the quantity of dose remaining in the drug delivery device 210 or the position of the actuator 214 (e.g., plunger) of the drug delivery device 210.

In some embodiments, the processing unit 260 can be configured to correct the signal signature for background noise. For example, the processing unit 260 can be configured to operate the sensing module 250 to detect a background signature with the lighting module in dark state, i.e., each of the plurality of light sources 244 switched off. The background signature can then be associated with the signal signature to correct for background noise. In some embodiments, the processing unit 260 can also include electronic signal filtering algorithms, e.g., Fourier transforms, low pass filter, band filter, high pass filter, Bessel filter, or any other digital filter to reduce noise and increase signal quality. The processing unit can also be configured to obtain reference signatures by storing the electromagnetic radiation signal detected by the sensing module 250 for a range of dose volumes in a representative drug delivery device 210, e.g., electromagnetic radiation signal at drug delivery device 210 full, empty and a series of intervals therebetween, e.g., every unit of dose dispensed from the drug delivery device and/or every 170 micrometer displacement of a plunger portion of the actuator 214 included in the drug delivery device 210.

Figure 18A:
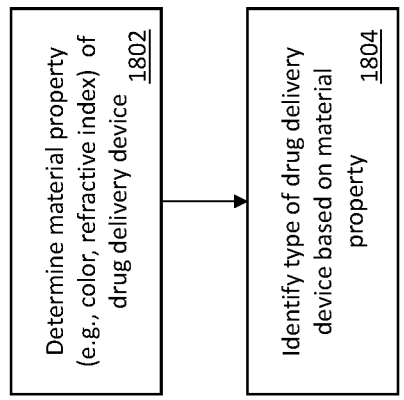
FIG. 18A and FIG. 18B are flow diagrams of a method of operation of the dose measurement system, according to an embodiment.
Figure 18B:
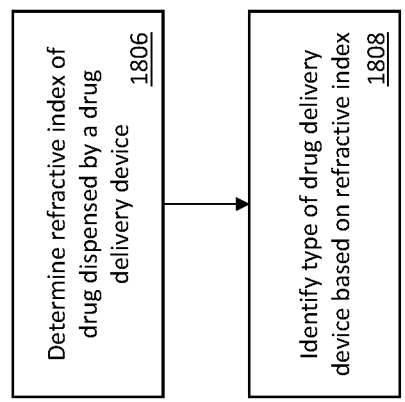

In some embodiments, the processing unit 260 can be configured to include probabilistic matching algorithms that can be used to associate the signal signature with the reference signature to determine a volume of liquid in the drug delivery device 210. In some embodiments, the processing unit 260 can also include algorithms to determine the type of drug delivery device 210 (e.g., as shown in FIG. 18A and FIG. 18B) coupled to the dose measurement system 200 and/or the drug contained within the drug delivery device 210, from the signal signature. For example, drug delivery devices 210 of the same form factor (i.e., size and shape) can include different drugs, for example, insulin, epinephrine, or any other drug. In order to avoid confusion, delivery device 210 manufactures often provide marking, labeling, or color coding to distinguish between different drugs in delivery devices 210 that look similar. Said another way, once a drug delivery device 210 company has designed and is manufacturing a particular delivery device 210, they often use that same design for different drug therapies. Therefore, in some embodiments, the algorithms included in the processing unit 260 can be configured to determine the type of drug delivery device 210 (e.g., at 1804 in FIG. 18A) coupled to the dose measurement system 200 based on, for example, material properties (e.g., color, refractive index, etc.) of the device (e.g., at 1802 in FIG. 18A). For example, different materials and/or colors can have different refractive indexes, which can be used for identification. In some embodiments, the type of drug included in the drug delivery device 210 can also be used to determine the type of delivery device 210 (e.g., at 1808 in FIG. 18B) based on the refractive index of the drug (e.g., at 1806 in FIG. 18B).

The processing unit 260 can also be configured to control and operate the communications module 270. In some embodiments, the processing unit 260 can be configured to operate the system in a power efficient manner. For example, the processing unit 260 can turn of the electronics powering the light sources 244, e.g., operational amplifiers when they are not needed. The processing unit 260 can pulse the LEDs for a short period at high current e.g., to save power and increase signal to noise ratio. The processing unit 260 can also be configured to periodically activate the communications module 270, e.g., 10 times per day or when the dose measurement system 200 is attached to the drug delivery device 210, and/or turn it off when it is not needed. In some embodiments, the processing unit 260 can also include a global positioning system (GPS) e.g., to determine a current location of the dose measurement system 200.

The communications module 270 can be configured to communicate data to the user and/or an external device, for example, a smart phone application, a local computer, and/or a remote server. The communicated data can include, e.g., initial system activation, system ON/OFF, drug delivery device 210 coupled/uncoupled, injector attached/detached from drug delivery device 210, dose remaining, dose history, time, system or drug temperature, system location (GPS), drug delivery device 210 coupling/uncoupling data, drug expiration date, velocity at which drug is delivered, device collisions, device power remaining, step count, tampering with the system, any other user health information and/or any other usable data. In some embodiments, the communications module 270 can also be configured to receive data, for example, new calibration data, firmware updates, user health information (e.g., blood glucose levels, diet, exercise, dose information) and/or any other information input by the user, or communicated by an external device. The communications module 270 can include conventional electronics for data communication and can use a standard communication protocol, e.g., Wi-Fi, Bluetooth®, low powered Blue-Tooth®, Zigbee, USB, firewire, and/or near field communication, e.g., infrared. In some embodiments, the communications module 270 can be configured to periodically connect, e.g., 10 times per day, to the external device, e.g., a smart phone, to log any dose data stored in the onboard memory. In some embodiments, the communications module 270 can be activated on demand by the user.

Figure 5:
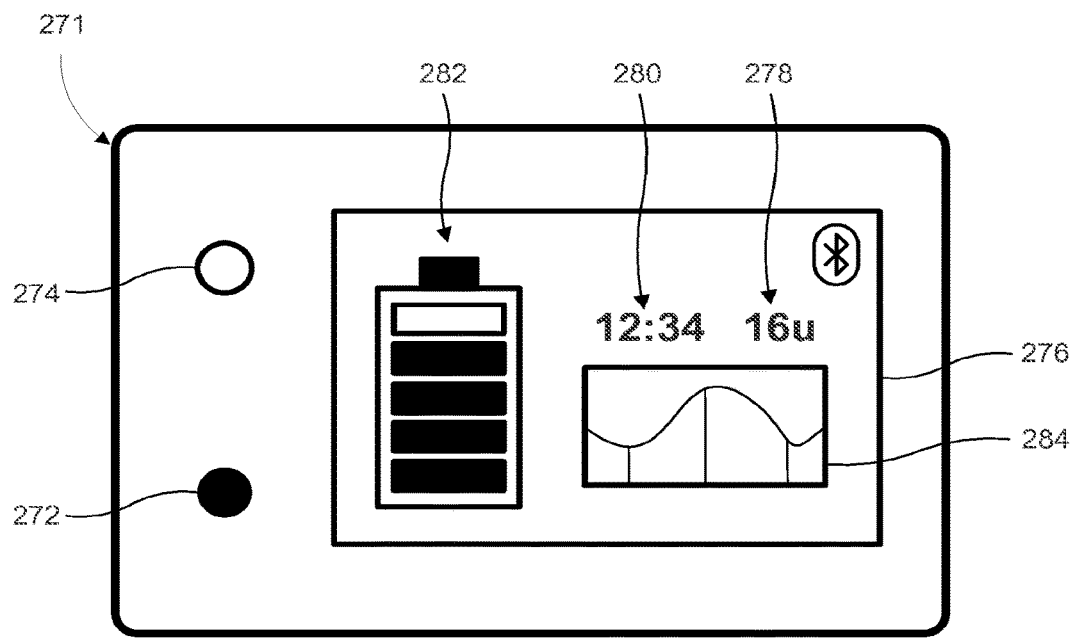
FIG. 5 is a schematic illustration of a communications interface that can be included in the dose measurement system of FIG. 2, according to an embodiment.

Referring now also to FIG. 5, in some embodiments, the communications module 270 can include a communication interface 271 located on an external surface of the housing 210 of the dose measurement system 200 for communicating with the user. The communication interface 271 can include a switch 272, e.g., a power switch, a reset button, and/or a communication switch to manually initiate communication with an external device, e.g., activate Bluetooth®. In some embodiments, the communications interface 271 can also include an indicator 274 such as a light source (e.g., an LED) to indicate to the user, for example, if the dose measurement system 200 is ON/OFF, or the communication module 270 is active. In some embodiments, the communication interface 271 can include a display 276 for visual communication of information to the user, e.g., the dose remaining 278 in the drug delivery device 210, the current time 280, system power remaining 282, dose history 284 such as, e.g., average dose usage, time last dose taken, etc, and/or wireless connectivity status. In some embodiments, the communications interface 271 can include an alphanumeric keypad, and/or a touch screen, for example, to allow a user to input information (e.g., food intake, exercise data, etc.) into the dose measurement system 200. In some embodiments, the communications module 270 can include a microphone for providing audible alerts or messages to the user, e.g., dose reminders, reinforcement messages, and/or a microphone for receiving audio input from the user. In some embodiments, the communications module 270 can include means for tactile alerts, e.g., a vibration mechanism. In some embodiments, the communications module 270 can communicate other information pertaining to user health, e.g., steps taken, calories burned, blood glucose levels, and/or any other information.

The power source 286 can be any power source that can be used to power the dose measurement system 200. In some embodiments, the power source 286 can include a disposable battery. In some embodiments, the power source 286 can include a rechargeable battery, e.g., a NiCad battery, a Li-ion battery, Li-polymer battery, or any other battery that has a small form factor, (e.g., of the type used in cell phones), and/or does not to be charged frequently, e.g., charged once per month. In some embodiments, the power source 286 can be charged using an external power source, e.g., though a power socket located on the housing 220 or through a communication interface of the communications module 270, e.g., a USB interface. In some embodiments, the power source 286 can be charged using solar energy and can include solar panels. In some embodiments, the power source 286 can be charged using kinetic energy and can include mechanical energy transducers.

Figure 6:
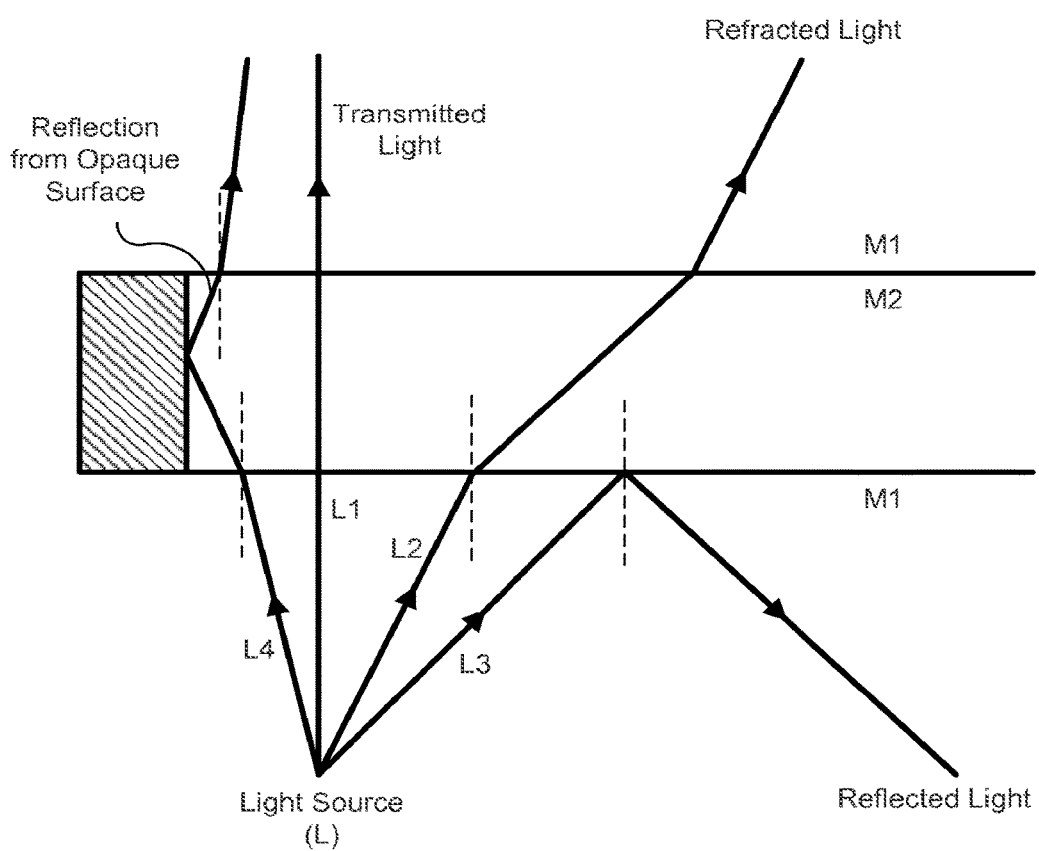
FIG. 6 is a schematic ray diagram of different modes of light transmission between a first medium and a second medium.

As described above, the plurality of sensors 254 of the sensing module 250 are configured to receive at least one of a transmitted radiation, refracted radiation, e.g., refracted through air, the liquid drug, the housing 212 of drug delivery device 210, reflected radiation, e.g., reflected from a wall of the housing 220 or internally reflected from a wall of the internal volume of the drug delivery device 210, or multi-directional reflection/refraction caused by a lensing effect of a curved surface of the housing 212 of the drug delivery device 210. Referring now to FIG. 6, a light source L (e.g., a wide angle light source) can produce a plurality of light rays emanating and diverging away from the light source. The light source L is present in a first medium M1 (e.g., air) having a first refractive index n1. A second medium M2 (e.g., liquid drug) having a second refractive index n2, greater than the first refractive index (i.e., n2>n1), is bordered by the first medium M1 on both sides. The second medium M2 can also include an opaque surface, e.g., a sidewall.

A first light ray L1 emitted by the light source L is incident on the interface of the first medium M1 and the second medium M2 at a first angle of 0 degrees. This light ray does not bend as it penetrates through the second medium M2 and transmits back into the first medium M1 (the transmitted light) at the original angle of incidence. A second light ray L2 is incident on the interface of the first medium M1 and the second medium M2 at a second angle >0. The second light ray L2 bends or refracts (the refracted light) as it penetrates the second medium M2, and then bends again to its original angle of incidence as it reenters the first medium M1, parallel to but offset from the emitted ray L2. A third light ray L3 is incident on the interface of the first medium M1 and the second medium M2 at a third angle greater than the second angle. At this angle of incidence, the light ray L3 does not penetrate into the second medium M2, but it is reflected back into the first medium M1 (the reflected light), such that angle of reflection is equal to the angle of incidence. A fourth light ray L4 is incident on the interface of the first medium M1 and the second medium M2 at a fourth angle less then the third angle, such that the light ray L4 refracts in the second medium M2, but is now incident on the opaque surface included in the second medium M2 (reflection from opaque surface). At least a portion of the light ray L4 is reflected back into the second medium M2, which then reenters back into the first medium M1 at a fifth angle, such that the fifth angle is not equal to the fourth angle.

As described herein, the electromagnetic radiation signal received by the plurality of sensors 254 of the sensing module 250 can include a combination of the transmitted, refracted and reflected portions of the electromagnetic radiation. A unique signal signature is produced by the combination of the portions of the electromagnetic radiation at different dose volumes remaining, and/or the actuator 216 position of the drug delivery device 210. This signal signature can be compared with a reference signal signature database (also referred to herein as "a calibration curve") to obtain the volume of dose remaining in drug delivery device 210, as described in further detail herein.

Figure 7:
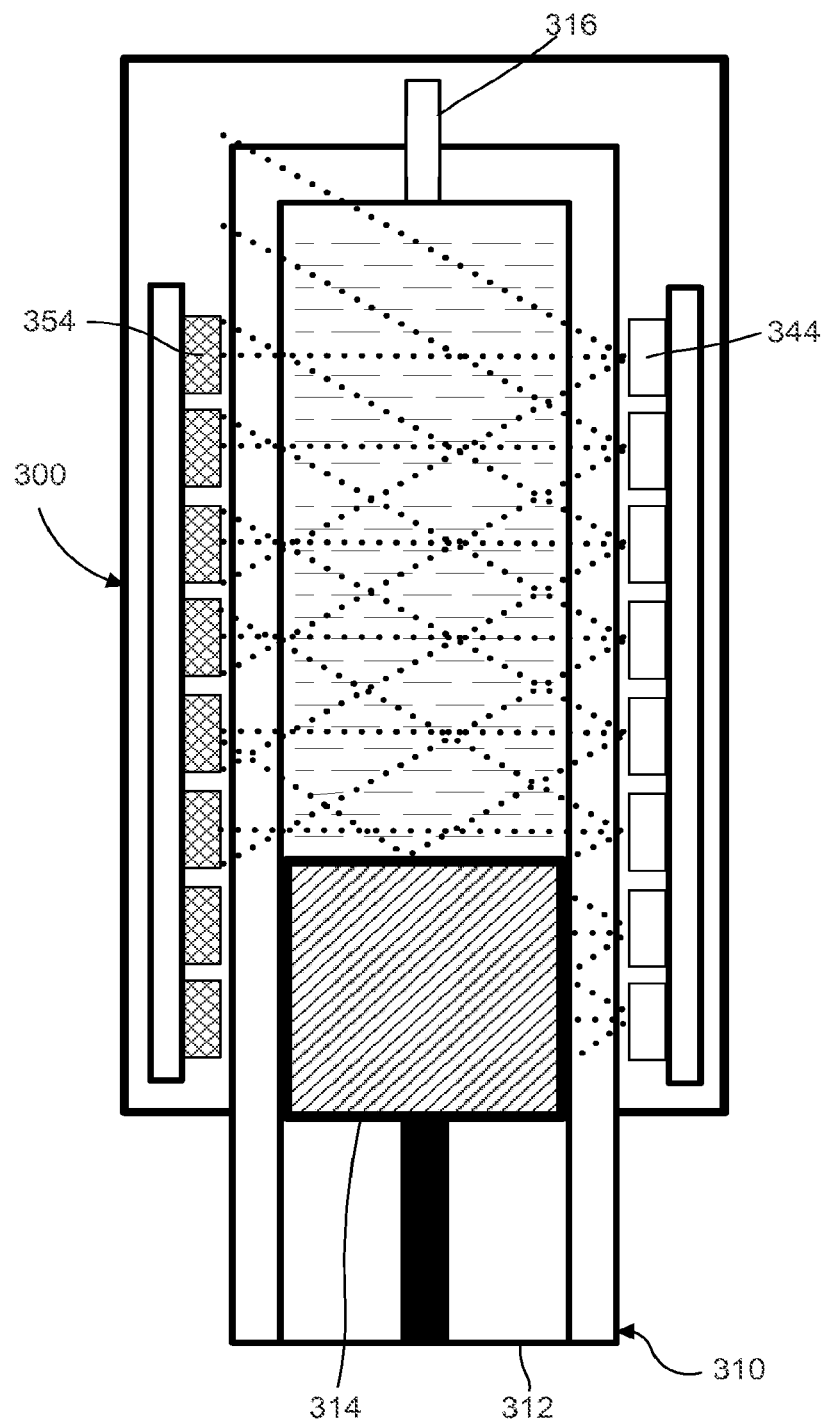
FIG. 7 is a cross-section view of a dose measurement system, according to an embodiment.

Referring now to FIGS. 7-10, various configurations of the light sources and the sensors are shown and described. While the transmitted and reflected portion of the electromagnetic radiation emitted by the light sources is shown, the refractive portion is not shown for clarity. As shown in FIG. 7, a dose measurement system 300 includes a plurality of light sources 344 and a plurality of sensors 354. A drug delivery device 310 is coupled to the dose measurement system 300. The drug delivery device 310 includes a housing 312 and an actuator 314 that collectively define an internal volume (e.g., reservoir) for containing a drug. The drug delivery device 310 also includes an injector 316 for communicating the drug to a patient. The dose measurement system 300 is configured such that the plurality of light sources 344 are disposed on a first side of the housing oriented towards the drug delivery device 310 and the plurality of sensors 354 are disposed on a second side of the housing such that each of the plurality of sensors 354 is substantially opposite to, and in optical communication with, at least one of the plurality of light sources 344. In some embodiments, the plurality of light sources 344 and/or the plurality of sensors 354 can be disposed in a substantially linear relationship (e.g., a straight line) with respect to each other. Each of the plurality of sensors 354 receive a combination of transmitted, refracted and reflected electromagnetic radiation emitted by the plurality of light sources 344. The reflection portion of the electromagnetic radiation can be reflected from a plunger portion of the actuator 314, and/or reflected from a housing of the dose measurement system 300 or the housing 312 of the drug delivery device 310. The refraction can be from the housing 312 and/or from the liquid drug disposed in the drug delivery device 310. The combination of the transmitted, reflected and refracted portions of the electromagnetic radiation detected by each of the plurality of sensors yields a unique signal signature for a range of dose volumes remaining in the drug delivery device 310.

Figure 8:
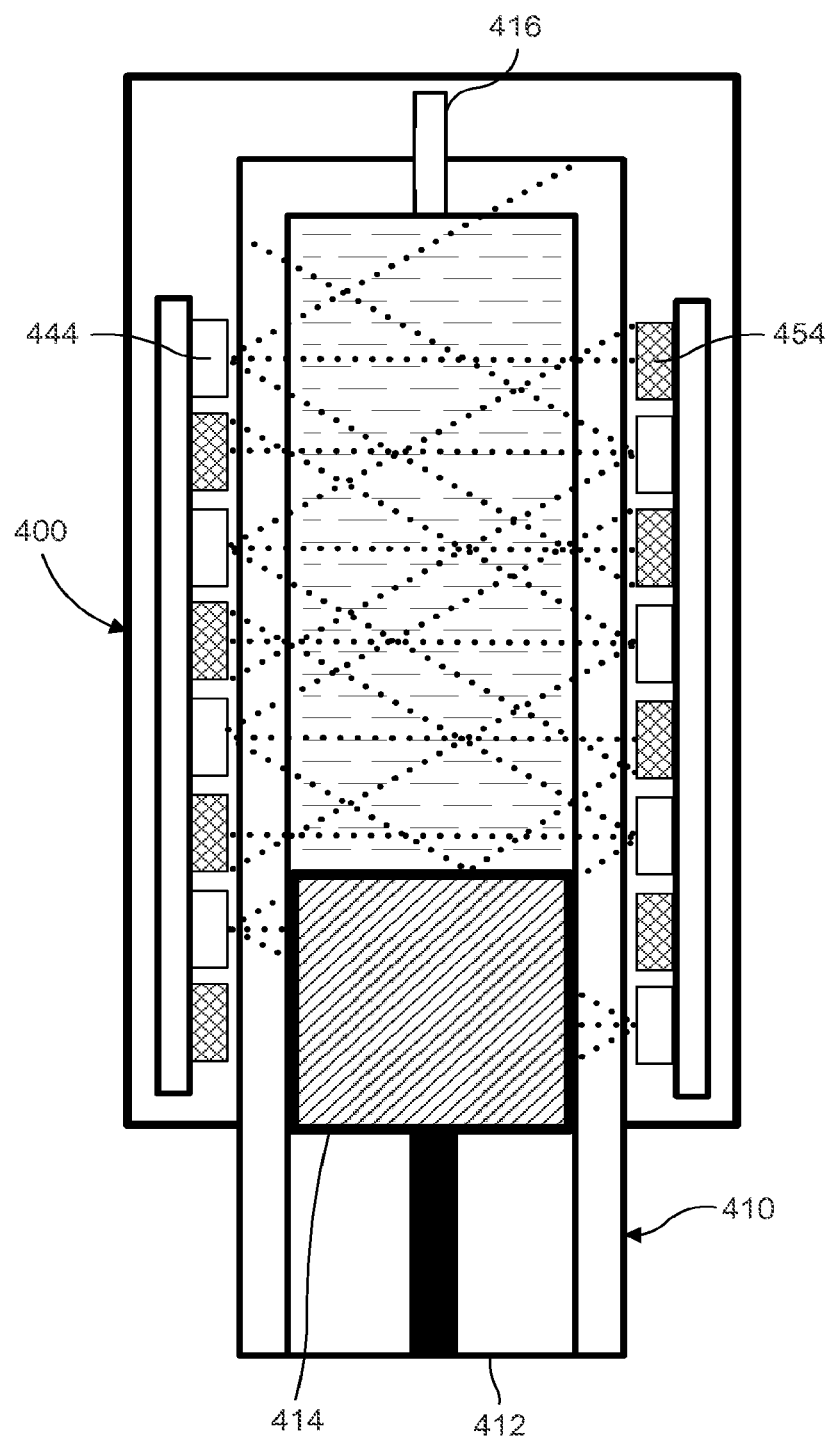
FIG. 8 is a cross-section view of a dose measurement system, according to an embodiment.

In some embodiments, a plurality of light sources and a plurality of sensors can be alternately disposed both sides of a drug delivery device. As shown in FIG. 8, a dose measurement system 400 includes a plurality of light sources 444 and a plurality of sensors 454. The drug delivery device 410 includes a housing 412 and an actuator 414 that collectively define an internal volume (e.g., reservoir) for containing a drug. The drug delivery device 410 also includes an injector 416 for communicating the drug to a patient. The dose measurement system 400 is configured such that the plurality of light sources 444 and the plurality of sensors 454 are disposed on both sides of the drug delivery device. In other words, each side of the drug delivery device 410 has a plurality of light sources 444 and a plurality of sensors 454. This can be advantageous as emission and detection of electromagnetic radiation is now performed from both sides of the drug delivery device 410, which can, for example, remove any biases.

Figure 9:
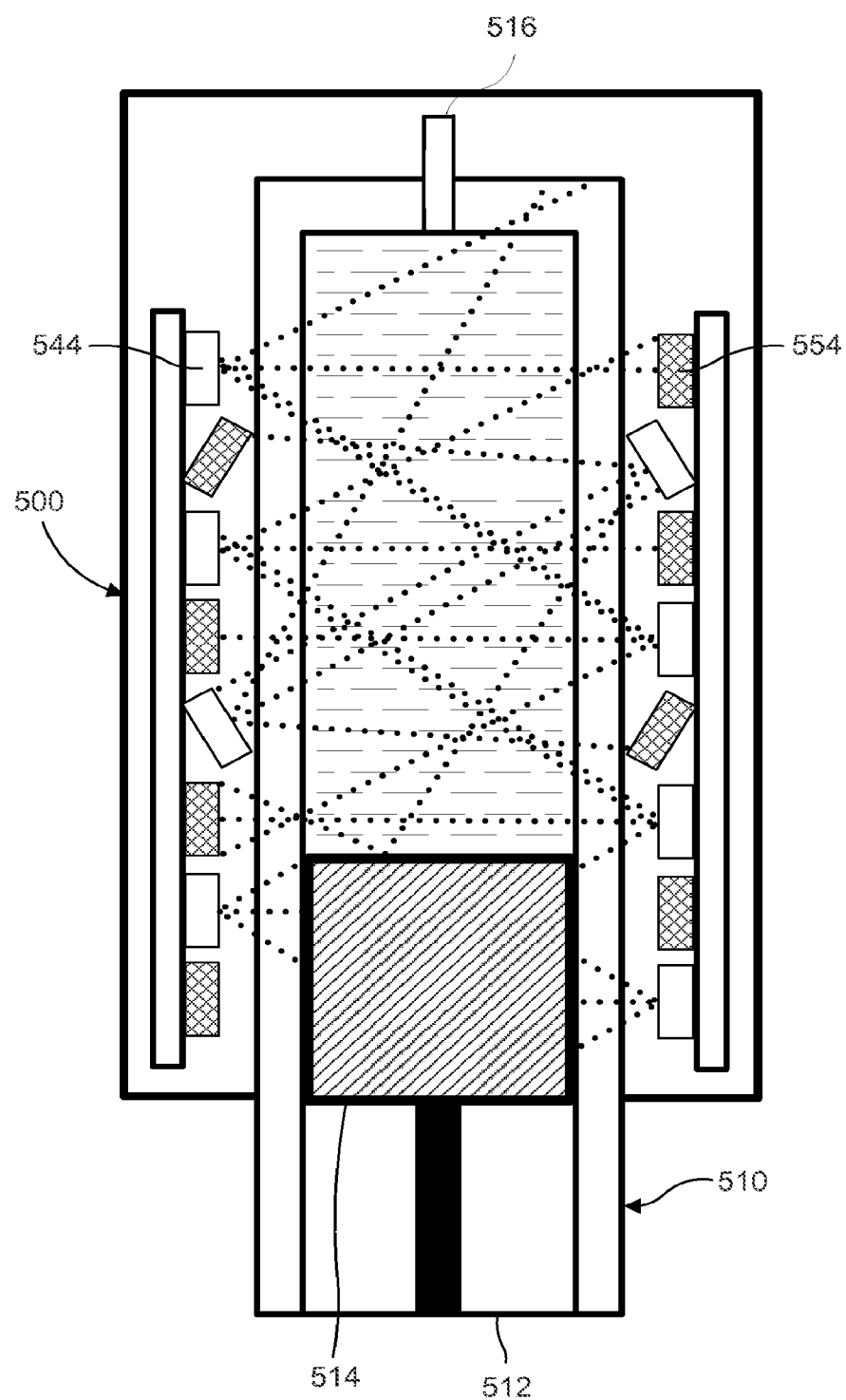
FIG. 9 is a cross-section view of a dose measurement system, according to an embodiment.

In some embodiments, at least a portion of the plurality of light sources and/or the plurality of sensors can be arranged in an angular orientation. As shown in FIG. 9, a dose measurement system 500 includes a plurality of light sources 544 and a plurality of sensors 554. The drug delivery device 510 includes a housing 512 and an actuator 514 that collectively define an internal volume (e.g., reservoir) for containing a drug. The drug delivery device 510 also includes an injector 516 for communicating the drug to a patient. The dose measurement system 500 is configured such that the plurality of light sources 544 and the plurality of sensors 554 are disposed on both side of the drug delivery device 510 and have an angular orientation with respect to a longitudinal axis of the dose measurement system 500 and drug delivery device 510. This orientation can ensure that the electromagnetic radiation emitted by the plurality of light sources 544 is incident on a larger portion of the drug delivery device 510 then can be achievable with a the light sources 544 oriented in a straight line. Similarly, the plurality of sensors 554 can also detect a greater portion of the electromagnetic radiation. This can, for example, result in higher resolution of the sensors 554, and/or reduce the quantity of light sources 544 and/or sensors 554 required to achieve the desired resolution.

In some embodiments, wider angle LEDs, for example, can also be used ensure that the electromagnetic radiation emitted by the plurality of light sources 544 is incident on a larger portion of the drug delivery device 510 than can be achievable with a narrower beam light sources 544. In other words, with a wider beam emitted by the light sources 544, a higher proportion of the overall drug delivery device 510 (or of the drug reservoir) is in optical communication with the light sources 544. Since a higher proportion of the delivery device 510 is in optical communication with the light sources 544, a broader spectrum of electromagnetic radiation being transmitted, reflected and/or refracted through the drug delivery device can increase the signal strength detectable by the plurality of sensors 554. Said other way, variability in the signal signatures (as opposed to increased intensity of light incident on the sensor) increases with the broadening of the beam of light incident on the delivery device, therefore increasing the resolution of the dose measurement system 500. For example, wider angles may increase ability to distinguish states of the drug delivery device, even though the overall intensity of light may be lower. This is because distinguishing states is more about optimizing how the intensity of light changes from state to state than it is about the absolute intensity of light.

Figure 10:
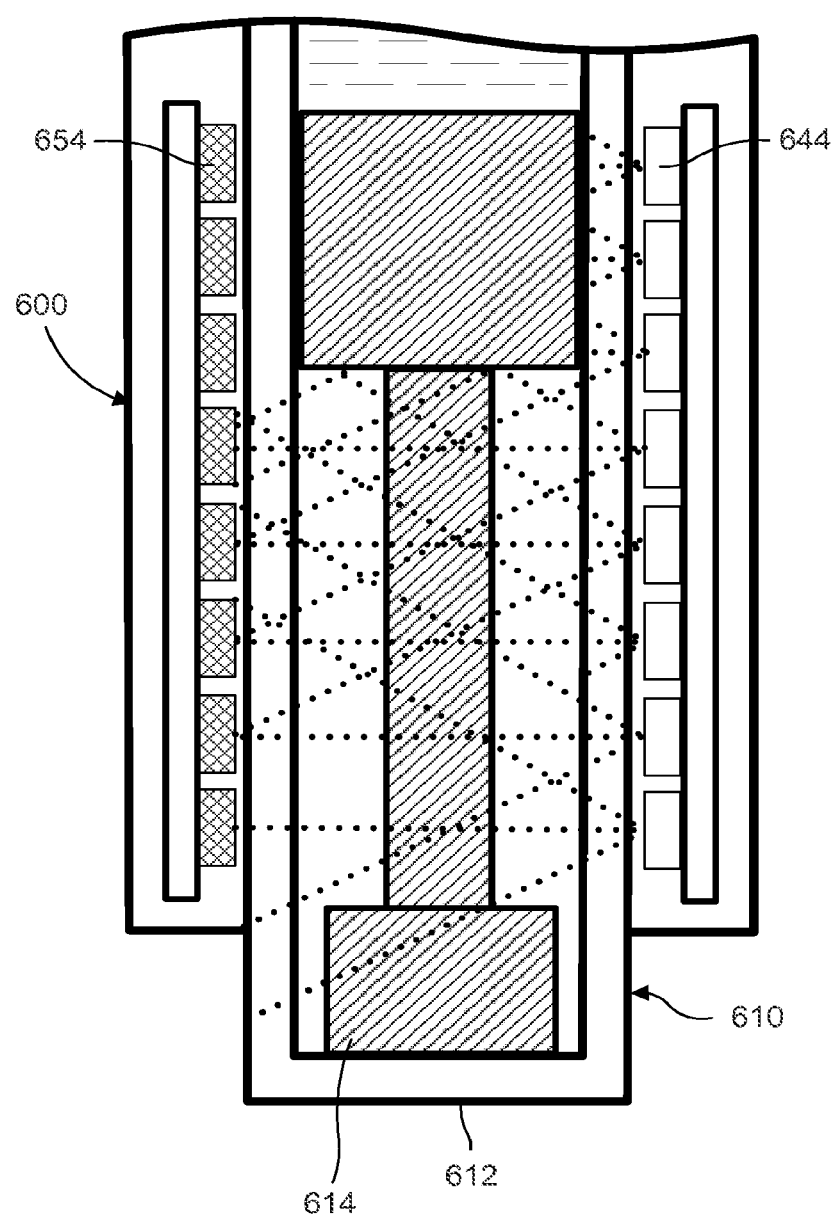
FIG. 10 is a side cross-section view of a dose measurement system, according to an embodiment.

In some embodiments, a dose measurement system can be configured to detect a signal signature from a location of an actuator of a drug delivery device, which can be used to estimate the dose remaining in the drug delivery device. As shown in FIG. 10, a dose measurement system 600 includes a plurality of light sources 644 and a plurality of sensors 654. A drug delivery device 610 is coupled to the dose measurement system 600. The drug delivery device 610 includes a housing 612 and an actuator 614 that collectively define an interior volume (e.g. reservoir) for containing a drug. The dose measurement system 600 is disposed generally about the actuator 614 portion of the drug delivery device 610 as opposed to the dose measurement systems 300, 400 and 500 being disposed generally around the drug reservoir as shown in FIGS. 7-9. The plurality of light sources 644 and sensors 654 are configured and arranged in a substantially similar way as described above with reference to FIG. 7. Electromagnetic radiation emitted by the plurality of light sources 644 can be transmitted unblocked by the actuator 614, blocked by a plunger portion of the actuator 614, reflected by a body or the plunger portion of the actuator 614 and/or reflected/refracted by the housing the drug delivery device 610. The combination of the transmitted, reflected and refracted portions of the electromagnetic radiation detected by the plurality of sensors 654 are then used to generate a signal signature at a given position of the actuator 614. Displacement of the actuator 614 from a first position to a second position changes the transmission, reflection and refraction pattern of the electromagnetic radiation detected by the sensors 654, creating a unique signal signature at each position of the actuator 614. This signature can be correlated to the dose volume remaining in the drug delivery device 610, e.g., by association with a reference signature.

Figure 11B:
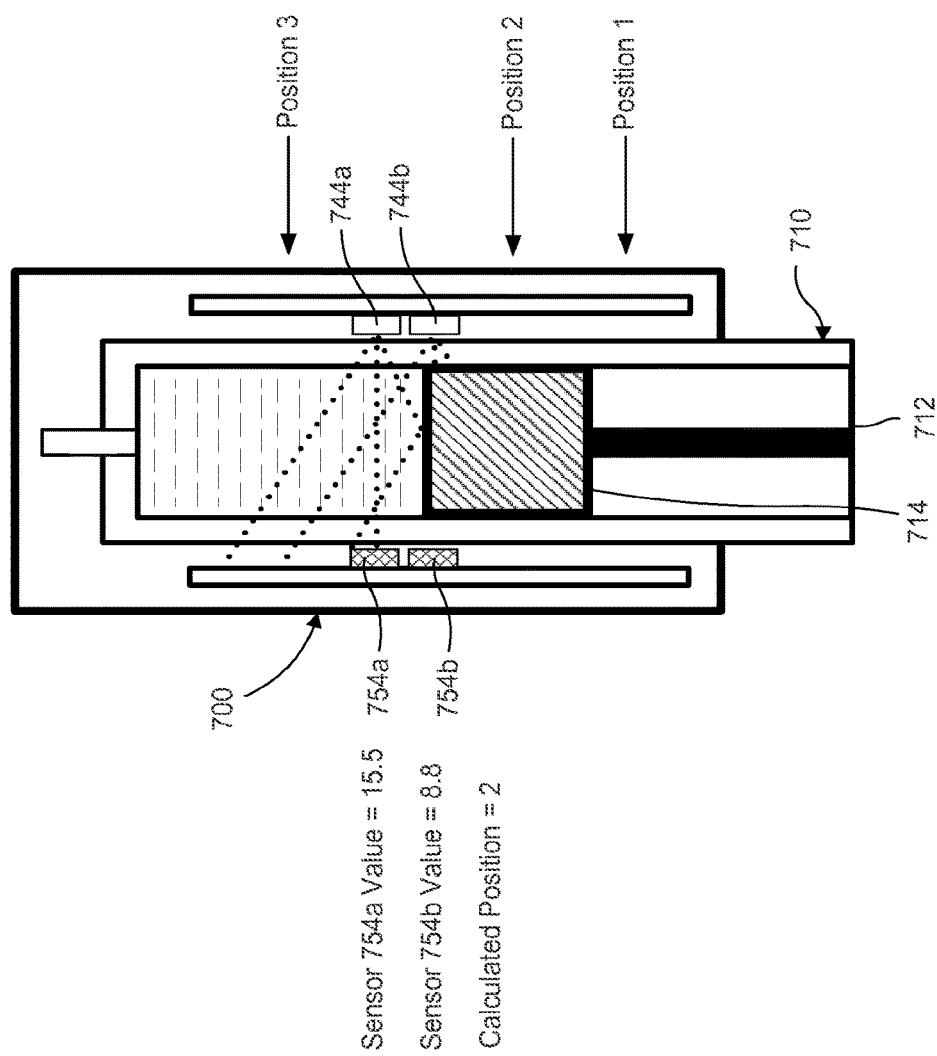

Referring now to FIGS. 11A-11C, each sensors of the plurality of sensors of a dose measurement system can detect the electromagnetic radiation emitted by at least a portion of the plurality of light sources, and the detected electromagnetic radiation can be a combination of transmitted reflected and refracted electromagnetic radiation. As shown, the dose measurement system 700 includes two light sources 744a and 744b, and two sensors 754a and 754b for clarity. The dose measurement system 700 is coupled to a drug delivery device 710 which includes a housing 712 and an actuator 714 that collectively define an internal volume (e.g., reservoir) for containing a liquid drug. The drug reservoir and at least a plunger portion of the actuator 714 are disposed substantially inside the dose measurement system 700 between the light sources 744a, 744b and sensors 754a, 754b.

As shown in FIG. 11A, the plunger portion of the actuator 714 is in a first position (position 1) such that the plunger portion is not in the line of sight of light sources 744a and 744b and sensors 754a and 754b. When electromagnetic radiation is emitted by the light sources 744a and 744b towards the drug delivery device 710, a significant portion of the electromagnetic radiation is detected by the sensors 754a and 754b in position 1. The electromagnetic radiation can include transmitted radiation, reflected radiation (e.g., by the housing 712 of the drug delivery device 710) and refraction, (e.g., by the liquid drug and/or housing), and multi-direction reflection/refraction because of a curved surface of the housing 712 of the drug delivery device 710 as described in more detail below. As shown in this example, sensor 754a value is 15.3 and sensor 754b value is 13.7, which indicates that a significant portion of the electromagnetic radiation is detected by the sensors 754a and 754b.

As shown in FIG. 11B, the actuator is 714 has been displaced to a second position (position 2) such that the plunger portion partially blocks the line of sight between the light source 744b and the sensor 754b. In position 2, a significant portion of the electromagnetic radiation emitted by the light source 744b is blocked from reaching the sensor 754b by the actuator 714, but at least a portion of the electromagnetic radiation emitted by light source 744a can still reach the sensor 754b along with any multi-directional reflected/refracted electromagnetic radiation. Furthermore, Sensor 754a can receive refracted electromagnetic radiation from sensor 744b and transmitted, refracted radiation from Sensor 744a. It also receives electromagnetic radiation reflected by a surface of the plunger that at least partially defines the drug reservoir. Therefore, at position 2 the sensor 754a detects an electromagnetic radiation value of 15.5 (greater than position 1), and sensor 754b detects an electromagnetic radiation value of 8.8 (less than position 1). The unique values measured at position 2 can serve as the signal signature values for position 2.

As shown in FIG. 11C, the plunger portion of the actuator 714 is in a third position (position 3) such that the plunger portion of the actuator 714 completely blocks the line of sight of the sensor 754a from the electromagnetic radiation emitted by light source 744a, such that substantially no transmitted and or reflected radiation from light source 744a can reach the sensor 754a. A portion of the transmitted electromagnetic radiation emitted by the light source 744b is also blocked by at least a portion of the actuator 714, from reaching the sensor 754b. Both the sensors 754a and 754b can still receive at least a portion of the reflected and refracted portions of the electromagnetic radiation emitted by any of the light sources 744a and/or 744b. Therefore, at position 3 the sensor 754a detects an electromagnetic radiation value of 2.2 (less than positions 1 and 2), and sensor 754b detects an electromagnetic radiation value of 12.0 (less than position 1, but greater than position 2). The unique values measured at position 3 can serve as the signal signature values for position 3.

Figure 12:
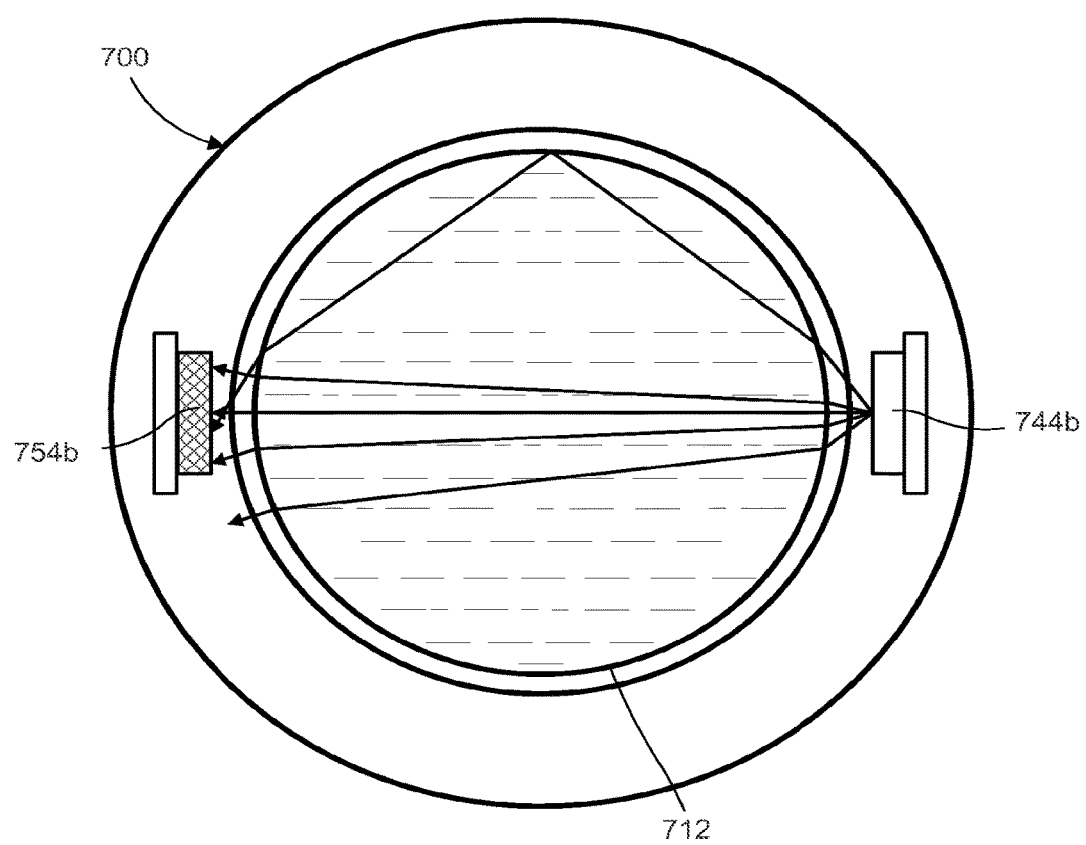
FIG. 12 is a cross-section view of the dose measurement system of FIG. 11A taken along line A-A

Referring now to FIG. 12, a cross section of the dose measurement system 700 taken along line AA in FIG. 11A is shown to illustrate the lensing effect caused by the curvature of the drug reservoir. As shown, a light ray emitted at a zero degree angle by light source 744b is transmitted without bending towards the sensor 754b. Two more light rays emitted by the light source 744b, at an angle away from the transmitted ray, are caused to refract (bend) towards the transmitted ray as they enter the drug reservoir because the liquid drug has a higher refractive index than air. This phenomenon is referred to herein as "a lensing effect," which can result in focusing of the light rays towards the sensor 754b. A fourth ray is emitted at an angle further away from the transmitted ray such that it refracts at the air/drug interface, and then is further reflected by an internal surface of the housing 712 of the drug delivery system 710 such that it is incident on the sensor 754b. A fifth ray is emitted at an angle, such that even after refrac not incident on the sensor 754b. As described above, the combination of these rays yields a detected electromagnetic radiation value of 15.3 by sensor 754a and 13.7 by sensor 754b. These unique values measured at position 1 can serve as the signal signature values for position 1.

Figure 13:
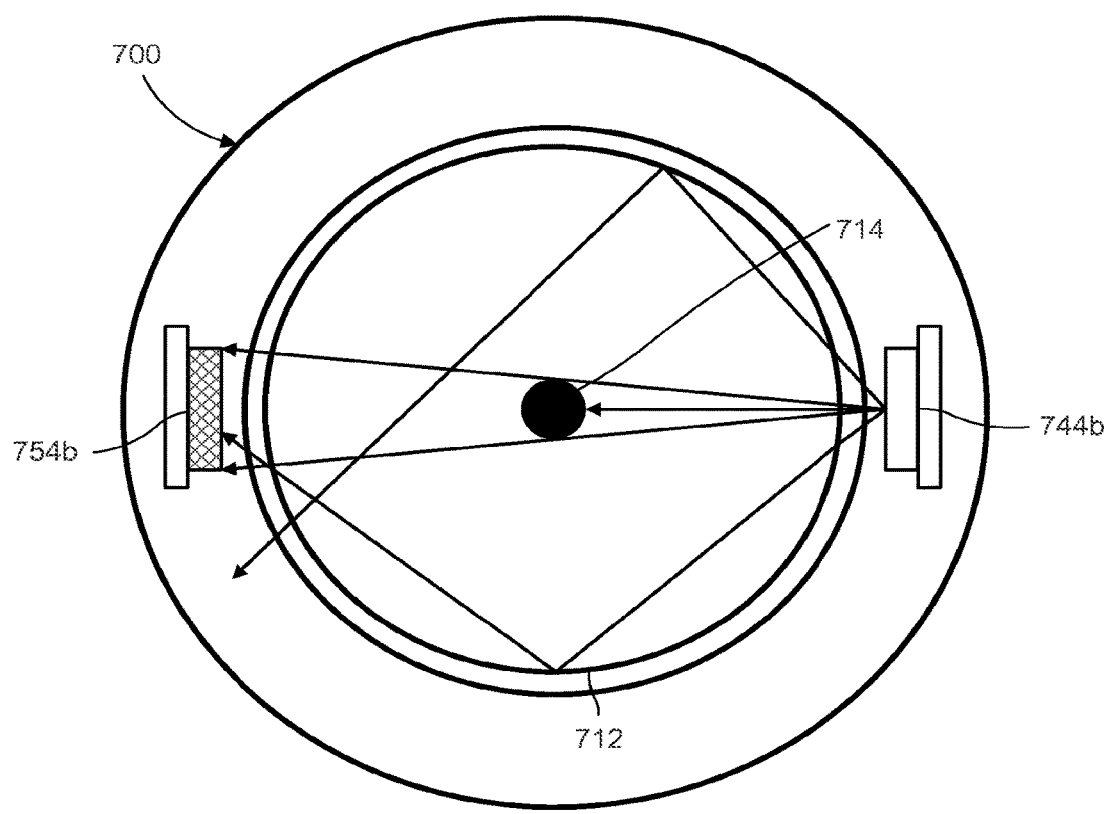
FIG. 13 is a cross-section view of the dose measurement system of FIG. 11C taken along line B-B.

Referring now to FIG. 13, a cross section of the dose measurement system 700 taken along line BB in FIG. 11C is shown to illustrate effect of the actuator 714 on the transmission of light. As shown, a light ray emitted at a zero degree angle by light source 744b is blocked by a portion of the actuator 714. Two more light rays emitted by the light source 744b, at an angle away from the transmitted ray, pass unrefracted (refraction through the housing is ignored) through the portion of the housing 712 of the drug delivery device 710 (there is no drug in this portion of the device 710) and are incident on the sensor 754b. A fourth ray is emitted by the light source 744b at an angle, such that it is internally reflected by the housing 712 and is incident on sensor 754b, while a fifth ray is internally reflected by the housing 712 but is not incident on the sensor 754b. The combination of these rays yields a detected electromagnetic radiation value of 2.2 by sensor 754a and 12.0 by sensor 754b. These unique values measured at position 3 can serve as the signal signature values for position 3. It is to be noted that although the line of sight of sensor 754a is completely blocked from light source 744a, reflected and refracted portions of the electromagnetic radiation still contribute to generation of a positive value.

Although the sensor values for particular positions are described as being absolute values, individual sensor values relative to other sensor values can be used to infer and/or determine the volume of liquid remaining in the drug reservoir. For example, sensor 754a having a particular value that is different from sensor 754b value by a certain amount or a certain percentage can be indicative of a position/drug volume remaining. Furthermore, a sensor value relative to two or more other sensor values can be used to generate a calibration curve of a drug delivery device 710.

Figure 14:
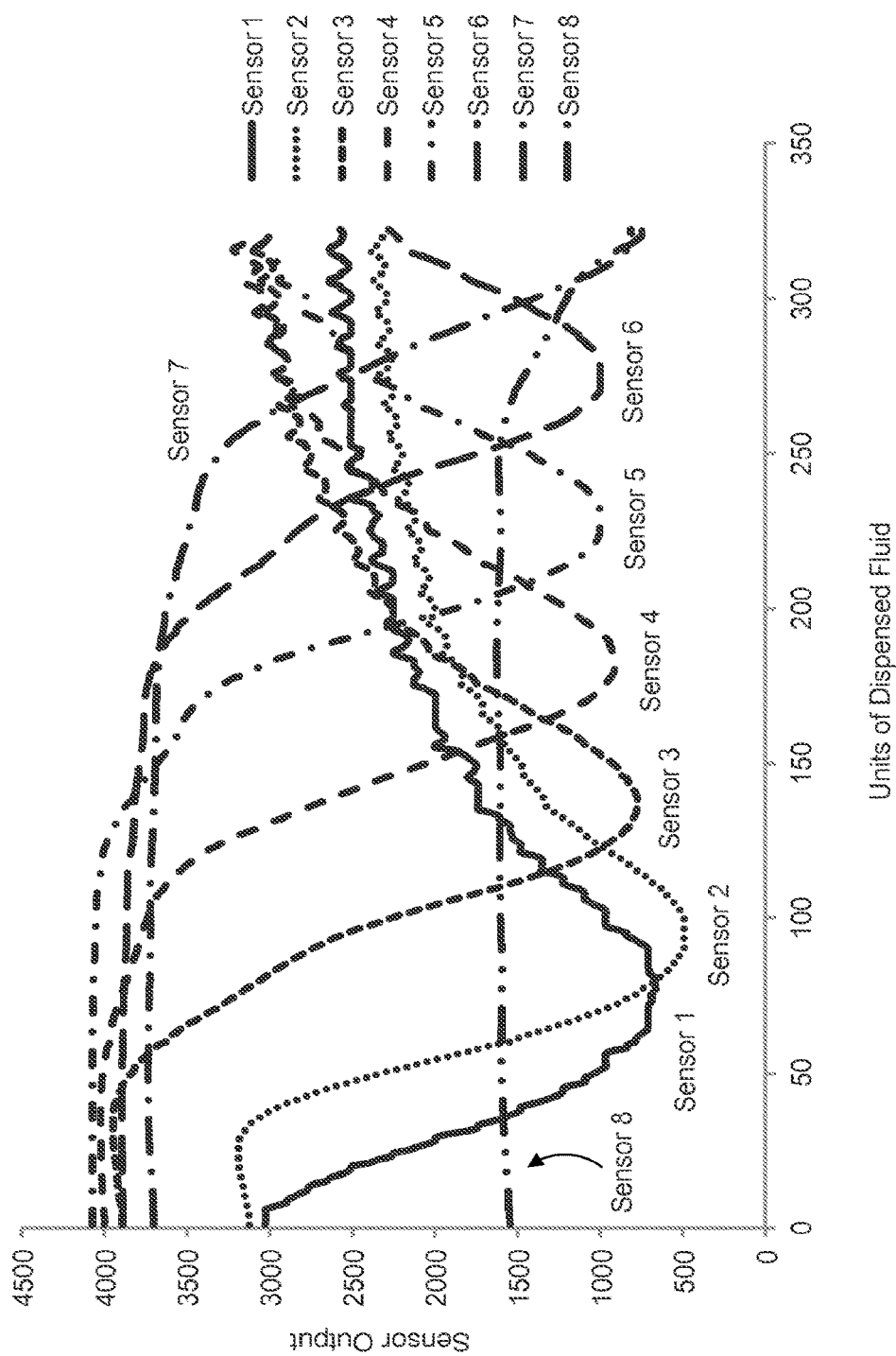
FIG. 14 shows reference signature signals of sensors of a dose measurement system, according to an embodiment.

A unique signal signature obtained at various configurations pertaining to the volume of dose dispensed by a drug delivery device can be used to obtain a reference signature (calibration curve) of the dose measurement system. FIG. 14 shows an example of a reference signal signature obtained for a drug delivery device using a dose measurement system that includes a total of seven sensors. The dose measurement system can be any dose measurement system as described herein. The electromagnetic radiation signature detected by each of the plurality of sensors for a range of dose volumes dispensed is stored and used to create the reference signature. As can be seen from the reference signature when the drug delivery device is almost full, sensor 1 records low amplitude of electromagnetic radiation, while sensor 7 records very high amplitude of electrode and all other sensors detect some intermediate signal signature. In contrast, when the drug delivery is completely empty, sensor 1 records very high amplitude of electromagnetic radiation, while sensor 7 records low amplitude and all other sensors detect some intermediate signal signature.

Sensor 8 detects a uniform sensor signal for a substantial portion of the dose delivered, until the almost all the dose has been delivered or the drug delivery device is almost empty. In some embodiments, the sensor 8 can also be used as the volume critically low sensor, e.g., to indicate that the drug delivery device is completely empty. In some embodiments, the sensor 8 can also be used as a usability metric sensor, e.g., to detect if a drug delivery device is coupled to the dose measurement system and/or an injector included in the drug delivery device is present or not.

Therefore in this manner, the signal value recorded from all sensors for a range of drug volumes remaining yields the signal signature for the entire volume of drug in the drug delivery device. The range of drug volumes used for obtaining the signal signature can include e.g., drug delivery device completely full, drug delivery device completely empty, and a sufficient number of intermediate signatures e.g., a signature obtained every unit of the total fluid dispensed, inclusive of all percentages therebetween.

In some embodiments, the reference signature can be corrected for background light. For example a background signature can be detected by detecting the signal signature from the plurality of sensors in a dark state of the plurality of light sources. The signal signature can be compared with the background signature to remove background noise. In some embodiments, the signal signature is associated with the reference signature to determine a drug volume in the drug delivery device, using probabilistic matching algorithms. In some embodiments, the plurality of light sources and the plurality of sensors can be configured such that the dose measurement system can detect the volume of drug in the drug delivery device with a resolution of 1 unit of drug, and/or position of a plunger portion of an actuator disposed in the drug delivery device 110 with a resolution of 100 micrometers, 110 micrometers, 120 micrometers, 130 micrometers, 140 micrometers, 150 micrometers, 160 micrometers, 170 micrometers, 180 micrometers, or 200 micrometers, inclusive of all ranges therebetween.

Figure 15:
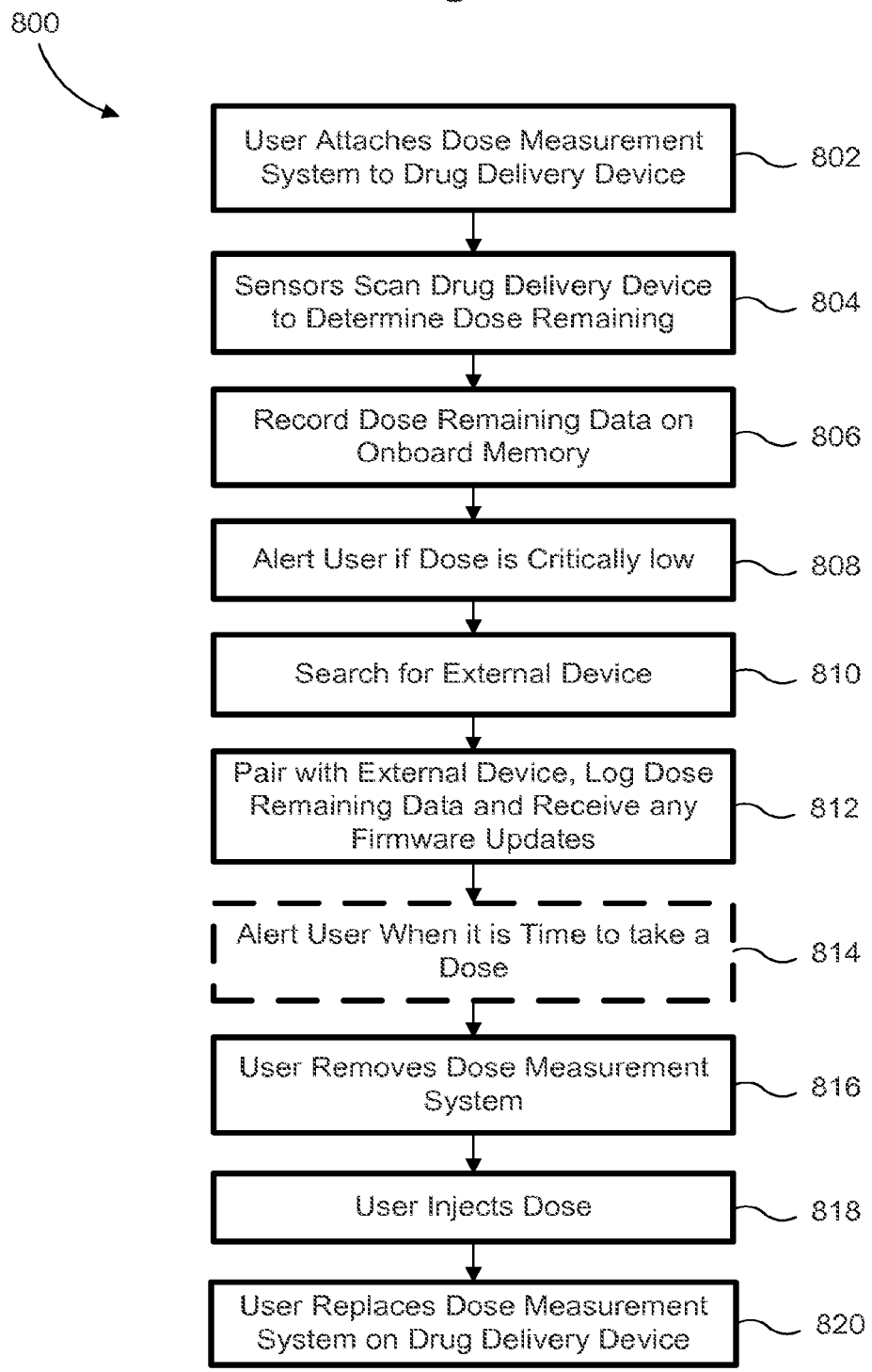
FIG. 15 is a flow diagram of a method of operation of the dose measurement system, according to an embodiment.

FIG. 15 illustrates a flow diagram showing a method 800 for measuring dose remaining in a drug delivery device using any of the dose measurement systems described herein. A user attaches a dose measurement system to a drug delivery device 802. A plurality of sensors disposed in the dose measurement system scan the drug delivery device to determine the dose remaining 804. For example, a processing unit of the dose measurement system can associate the signal signature detected by the plurality of sensors with a reference signature to determine the dose remaining. The sensor data is recorded on an onboard memory 806, e.g., an RFID chip and/or a memory that is part of the processing unit of the dose measurement system. The dose measurement system alerts the user if the dose remaining is critically low 808. Any one of audio, visual or tactile alerts can be used to alert the user. A communications module of the dose measurement system searches for an external device 810. For example, a Bluetooth® connection can be activated to search for the external device, e.g., a smart phone app, a local computer or a remote server. The dose measurement system pairs with the external device and logs dose remaining data on the external device and/or receives any firmware updates 812. Optionally, the dose measurement system can also alert a user when it is time to take a dose 814. After dose data has been recorded and transmitted to an external device, the user can remove the dose measurement system from the drug delivery device 816. The user then injects a pre determined volume of the dose using the drug delivery device 818. The user finally replaces the dose measurement system on the drug delivery device 820. The method 800 can then be repeated.

Figure 16:
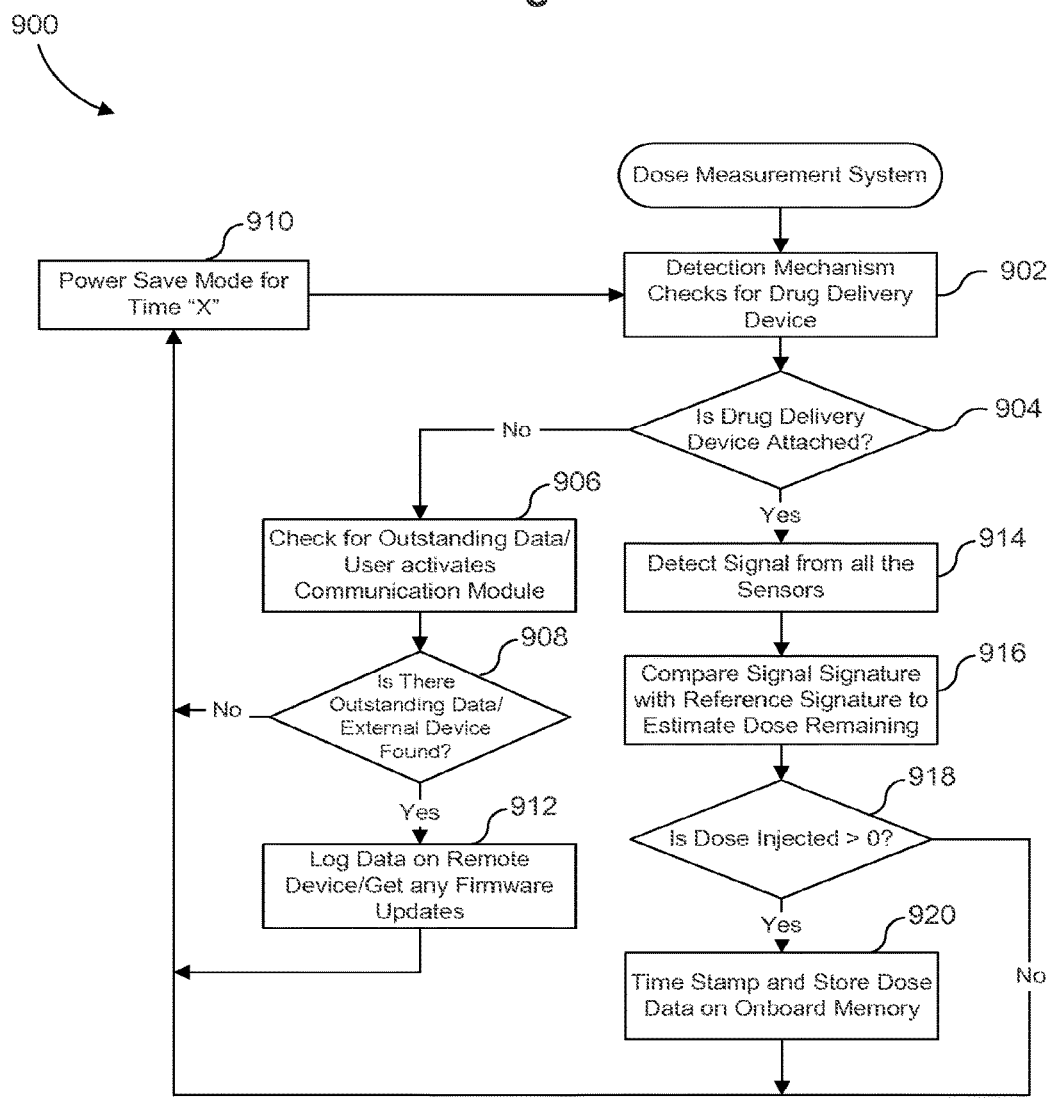
FIG. 16 is a flow diagram of a method of operation of the dose measurement system, according to an embodiment.

FIG. 16 illustrates a flow diagram showing a method 900 for conserving power when the dose measurement system is not in use. The method 900 described herein can be used with any of the dose measurement systems described herein. In a first step, a detection mechanism of the dose measurement system checks for a drug delivery device 902. The drug delivery device can either be coupled or uncoupled to the dose measurement system 904. If the drug delivery device is not attached, the dose measurement system automatically checks for outstanding data in the memory to be logged to an external device or the user can activate a communications module of the dose measurement system 906. In some embodiments, the communications module is only activated when the dose measurement system is attached to a drug delivery device. The dose measurement system then determines if there is onboard data to be logged and if an external device was found 908. If there is no onboard data to be logged and no external device was found, the dose measurement system goes into a power save mode for a pre-defined time "X" 910. For example, a processing unit of the system can turn off a communications module of the dose measurement system and/or turn off the electronics controlling a plurality of light sources and/or plurality of sensors of the dose measurement system. Time "X" can be, e.g., 1 minute, 10 minutes, 1 hour, or any time therebetween. Alternatively, if there is data to be logged and an external device was found, the dose measurement system pairs with the external device and logs data on the external device and/or receives any firmware updates from the external device 912. The dose measurement system can then go into the power save mode 910. If instead a drug delivery device was found to be attached to the dose measurement system 904, the dose measurement system scans the drug delivery device and collects signal from all of the plurality of sensors 914. The signal from each of the plurality of sensors can be used to create a signal signature corresponding to the dose remaining in the drug delivery device. A processing unit of the dose measurement system compares the signal signature with a reference signature to estimate dose remaining in the drug delivery device 916. The dose measurement system determines if the dose injected was greater than zero 918. If the dose injected was greater than zero, the dose measurement system time stamps and stores the dose on an onboard memory 920. The dose measurement system then goes into the power save mode for the time "X" 910. If the dose injected was not greater than zero 918, than the dose measurement system directly goes into the power save mode for the time "X" 910.

Figure 17:
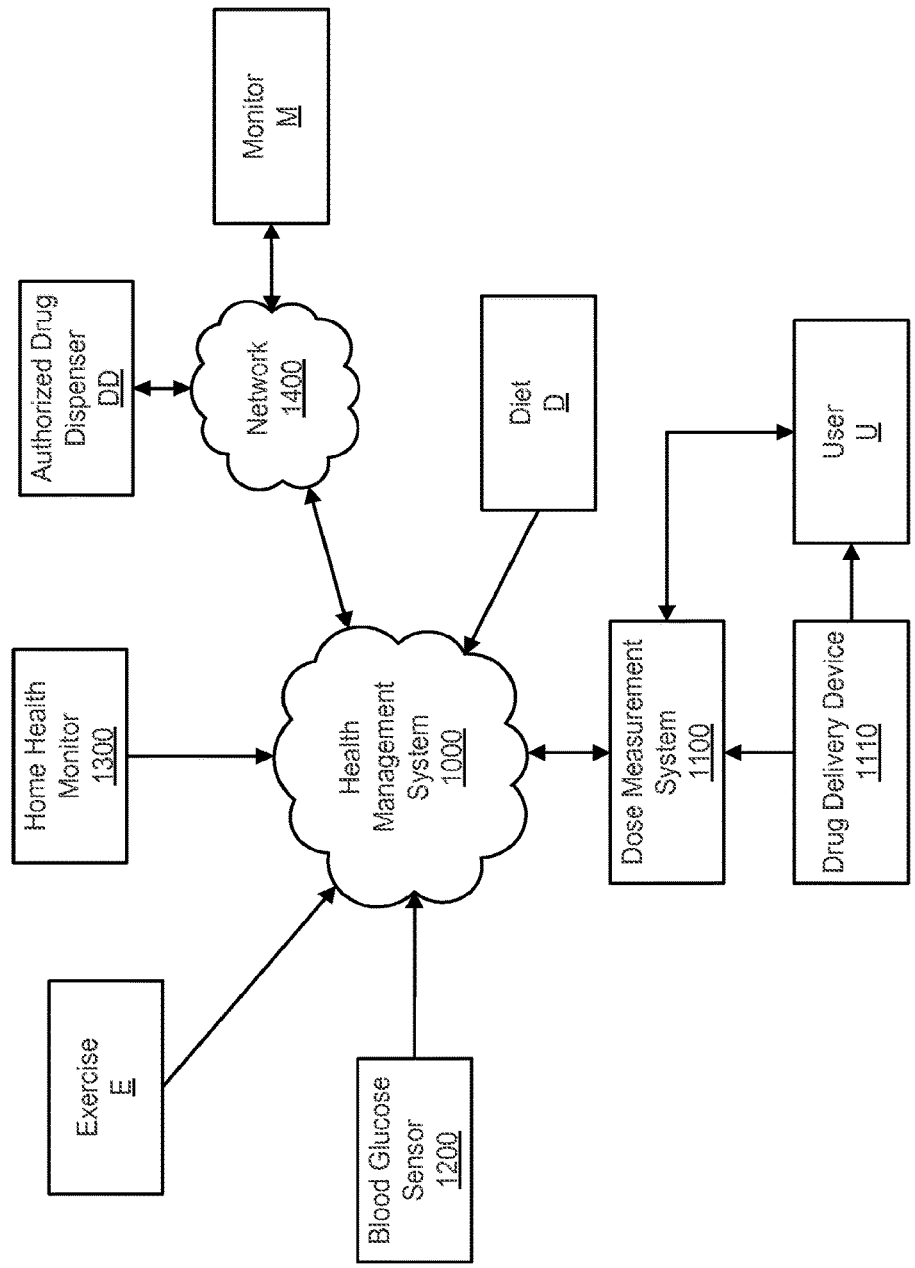
FIG. 17 is a schematic block diagram of a health management system associated with a dose measurement system, according to an embodiment.

In some embodiments, any of the dose measurement systems described herein can be associated with a health management system to manage the health of a patient suffering from Type I or II diabetes. FIG. 17 shows a schematic block diagram of a health management system 1000 for managing the health of a diabetic user U. In some embodiments, the health management system can be a smart phone application. In some embodiments, the health management system can be a local computer or a remote server. The health management system is in two way communication with a dose measurement system 1100 that can be reversibly coupled to a drug delivery device 1110. The drug delivery device 1110 can be an insulin injection pen or syringe for administering insulin to a user U. The dose measurement system can also communicate information to a user or receive an input from the user. The health management system 1000 is configured to receive the user exercise data E and diet data D. The health management system 1000 is also configured to receive blood glucose data from a blood glucose sensor 1200. The health management system 1000 can further be configured to receive user health data from a home health monitor 1300, e.g., weight, blood pressure, EKG, oxygen saturation, actigraphy measures, pulmonary function, water retention, temperature, etc. The health management system 1000 can be in two way communication with a network 1400. The network can be, for example, a remote server or a call center. The network 1400 can also be in two way communication with a monitor M and an authorized drug dispenser DD. The monitor M can be a doctor, a care giver, a pharmacy, and/or a clinical trial manager. The authorized drug dispenser DD can be a pharmacy or a clinical trial manager.

In some embodiments, the dose measurement system 1100 communicates to the health management system the insulin dose remaining in and/or the insulin dose delivered to the user U by the drug delivery device 1110. In some embodiments, the health management system can also include a memory for storing the user U insulin dose regimen and/or any other medication schedule. The user U medication regimen can be communicated to the health management system 1100 by, for example, the monitor M and/or the authorized drug dispenser DD through the network 1400. In some embodiments, the health management system 1100 can also be used to process user U health data, for example, user U blood glucose levels, exercise data E, diet data D, and/or home health monitored data to determine the status of patient health. In some embodiments, the health management system 1000 can also be configured to compare dose delivered to a patient with a patient medication schedule to monitor compliance. In some embodiments, the health management system can communicate the user health and dose information to the monitor M through the network 1400. The monitor M can analyze user U health data and determine if any changes to the patient medication plan, for example, insulin and/or any other medication dosage needs to be made. If a change is required, in some embodiments, the monitor M can communicate any changes to the user's U medication regimen to the authorized drug dispenser DD. In some embodiments, the monitor M can also communicate this information to the health management system 1100 through the network 1400. In some embodiments, the health management system 1100 can update and store the user U medication regimen and also communicate to the dose measurement system 1100, the user U new medication regimen. The user U can then access the dose measurement system 1400 to obtain the new measurement plan, for example, new insulin dosage. In this manner, a diabetic user's U health can be monitored and managed and the user's U medication schedule can be dynamically personalized to the user U. In some embodiments, health management system can also communicate the user U health and medication history on a periodic basis. The health and medication history can be used, for example, to inform the user U of any changes that need to be made to improve the user's U overall health. The medication history can also be communicated to the monitor M to analyze the user's U progressive health.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combination of components, other embodiments are possible having any combination or sub-combination of any features and/or components from any of the embodiments described herein. For example, although some embodiments were described as having a dose measurement system that resembled a pen cap, the dose measurement system can also be integrated with a drug delivery device. In some embodiments, vibration and/or ultrasonic waves can be used to generate the signal signature instead of electromagnetic radiation. In addition, the specific configurations of the various components can also be varied. For example, the size and specific shape of the various components can be different than the embodiments shown, while still providing the functions as described herein.

The invention claimed is:

1. A method of estimating volume of liquid ejected from a drug container, the method comprising:
   detecting electromagnetic radiation emitted by at least two of a plurality light sources with each of a plurality of sensors, the plurality of light sources emitting electromagnetic radiation toward the drug container, the drug container including an actuator;
   generating a signal signature representative of the electromagnetic radiation detected through the drug container by the plurality of sensors;
   comparing the signal signature to a plurality of reference signatures to determine a displacement of a plunger portion of the actuator; and
   determining the volume of the liquid ejected from the drug container based on the displacement of the plunger portion of the actuator.

2. The method of claim 1, further comprising:
   generating the plurality of reference signatures by recording a signal signature for each of a plurality of possible positions of the plunger portion of the actuator.

3. The method of claim 1, wherein the drug container is at least a part of a drug delivery device and a position of the plunger portion of the actuator indicates the volume of the drug dispensed by the drug delivery device.

4. The method of claim 3, further comprising:
   determining a material property of the drug delivery device; and
   identifying a type of the drug delivery device based on the material property.

5. The method of claim 4, wherein the material property of the drug delivery device is at least one of a color or a refractive index.

6. The method of claim 3, further comprising:
   determining a type of the drug delivery device based on a refractive index of the drug dispensed by the drug delivery device.

7. The method of claim 1, further comprising:
   communicating information associated with the dose delivered to an external device.

8. A method, comprising:
   causing at least two of a plurality of wide angle light sources to emit electromagnetic radiation toward a drug container in a dose measurement system;
   detecting the electromagnetic radiation emitted by the at least two wide angle light sources with each of a plurality of sensors; and
   generating a signal signature representative of the electromagnetic radiation detected through the drug container by the plurality of sensors.

9. The method of claim 8, wherein causing the at least two wide angle light sources to emit the electromagnetic radiation includes causing a broad spectrum of electromagnetic radiation to reflect, refract, and transmit through the drug container.

10. The method of claim 8, further including:
    comparing the signal signature to a plurality of reference signatures to determine a volume of liquid in the drug container.

11. The method of claim 10, further comprising:
    calculating a dose delivered to a patient based on the volume of liquid in the drug container.

12. The method of claim 8, wherein the plurality of wide light sources includes a plurality of adjacent wide light sources wherein at least a first portion of the electromagnetic radiation emitted by a first wide light source in the plurality of adjacent wide light sources overlaps with at least a second portion of the electromagnetic radiation emitted by a second wide light source in the plurality of adjacent wide light sources.

13. A method of estimating a volume of liquid in a drug container, the method comprising:
    detecting electromagnetic radiation emitted by at least two of a plurality of light sources with each of a plurality of sensors, the plurality of light sources emitting electromagnetic radiation toward the drug container;
    generating a signal signature representative of the electromagnetic radiation detected through the drug container by the plurality of sensors; and
    comparing the signal signature to a plurality of reference signatures to determine the volume of liquid in the drug container.

14. The method of claim 13, further comprising:
    calculating a dose delivered to a patient based on the volume of liquid in the drug container.

15. The method of claim 14, further comprising:
    communicating information associated with the dose delivered to an external device.

16. The method of claim 13, further comprising:
    generating the plurality of reference signatures by recording a signal signature of each of a range of dose volumes in the drug container.

* * * * *